United States Patent [19]

Higashijima et al.

[11] Patent Number: 5,589,568
[45] Date of Patent: Dec. 31, 1996

[54] METHODS AND COMPOSITIONS FOR MODULATING G PROTEIN ACTION

[75] Inventors: Tsutomu Higashijima; Elliott M. Ross, both of Dallas, Tex.

[73] Assignee: Board of Regents, The University of Texas, Austin, Tex.

[21] Appl. No.: 232,453

[22] Filed: Apr. 22, 1994

Related U.S. Application Data

[63] Continuation of Ser. No. 748,319, Aug. 21, 1991, abandoned.

[51] Int. Cl.$^6$ .......................... A61K 37/02; C07K 14/00; C07K 7/08
[52] U.S. Cl. .......................... 530/324; 530/325; 530/326; 530/327
[58] Field of Search .................................... 530/324–327; 514/12–14

[56] References Cited

PUBLICATIONS

Nishimoto et al., J. Biol. Chem., 266(19):12747–12751, 1991.
Dalman et al., J. Biol. Chem., 266(17):11025–11029, 1991.
Regoli & Nantel, Trends Pharmacol. Sci., 11:400–401, 1990.
Argiolas and Pisano, "Facilitation of Phospholipase A$_2$ Activity by Mastoparans, a New Class of Mast Cell Degranulating Peptides form Wasp Venom," *J. Biolog. Chem.*, 258(22):13697–13702, 1983.
Higashijima et al., "Mechanism of Histamine–Release by Mastoparan," *Peptide Chemistry* 1986, T. Miyazawa (Ed.), pp. 75–78, 1986.
Yajima et al., "Studies on Peptides. LXXXVI. Application of the Trifluoroacetic Acid–Thioanisole Deprotecting Procedures for the Synthesis of a Wasp Venom, Mastoparan," *Chem. Pharm. Bull.*, 28(4):1214–1218, 1980.
International Search Report, mailed Nov. 18, 1992.
Tomita, U. et al., "Direct Interactions of Mastoparan and Compound 48/80 with GTP–Binding Proteins," *J. Biochem.*, 109:184–189, 1991.
Tomita, U. et al., "Direct Activation of GTP–Binding Proteins by Venom Peptides that Contain Cationic Clusters Within Their Alpha–Helical Structures," *Biochem. and Biophys. Res. Com.*, 178(1):400–406, 1991.
Münch, G. et al., "Multisite contacts involved in coupling of the β–adrenergic receptor with the stimulatory guanine–nucleotide–binding regulatory protein," *Eur. J. Biochem.*, 198:357–364, 1991.
Rubinfeld, B. et al., "A synthetic peptide corresponding to a sequence in the GTPase activating protein inhibits p21$^{ras}$ stimulation and promotes guanine nucleotide exchange," *Int. J. Peptide Protein Res.*, 38:47–53, 1991.

Cheung, A. et al., "Specific activation of G$_s$ by synthetic peptides corresponding to an intracellular loop of the β–adrenergic receptor," *FEBS*, 279(2):277–280, 1991.
Higashijima, T. et al., "Regulation of G$_i$ and G$_o$ by Mastoparan, Related Amphiphilic Peptides, and Hydrophobic Amines," *J. Biol. Chem.*, 265(24):14176–14186, 1990.
Huang, R. et al., "Identification of Allosteric Antagonists of Receptor–Guanine Nucleotide–Binding Protein Interactions," *Mol. Pharmaco.*, 37:304–310, 1990.
Okamoto, T. et al., "A Simple Structure Encodes G Protein–Activating Function of the IGF–II/Mannose 6–Phosphate Receptor," *Cell*, 62:709–717, 1990.
Mousli, M. et al., "Direct activation of GTP–binding regulatory proteins (G–proteins) by substance P and compound 84/80," *FEBS*, 259(2):260–262, 1990.
König, B. et al., "Three cytoplasmic loops of rhodospin interact with transducin," *Proc. Natl. Acad. Sci. USA*, 86:6878–6882, 1989.
Higashijima, T. et al., "Mastoparan, a Peptide Toxin form WASP Venom, Mimics Receptors by Activating GTP–binding Regulatory Proteins (G Proteins)," *J. Biol. Chem.*, 263(14):6491–6494, 1988.
Alberts, B. et al., *Molecular Biology of the Cell*, Second Edition, Garland Publishing, Inc., New York & London, 1989, pp. 694–699; 705–708.
Darnel, J. et al., *Molecular Cell Biology*, Scientific American Books, Inc., New York, 1986, pp. 679–697.
Wakamatsu, K. et al., "Action Mechanisms of Mastoparan, A Wasp Venom Peptide," *Peptide Chemistry 1984*, Ed. N. Izumiya, Protein Research Foundation, Osaka, Japan, 1985, pp. 183–186.
Higashijima, et al, J. Biol Chem., 265(24): 14176–14186, 1990.
Okamoto, et al, *Cell*, 62:709–717, 1990.

*Primary Examiner*—Christina Y. Chan
*Assistant Examiner*—S. G. Marshall
*Attorney, Agent, or Firm*—Arnold, White & Durkee

[57] ABSTRACT

The present disclosure relates to methods and compositions for modulating the action of G proteins. G proteins are important to cellular regulation in all human cells and their function is involved in a wide variety of human disease processes. In particular aspects, the present disclosure concerns the development of mastoparan analogs as well as other amphipathic and cationic peptides, termed receptor-based analogues, that can promote activation of one or more G proteins, and are therefore proposed to be useful in the treatment of a variety of disorders including asthma, ulcers, cardiovascular diseases and even Parkinson's disease.

85 Claims, 6 Drawing Sheets

METHODS AND COMPOSITIONS FOR MODULATING G PROTEIN ACTION

The government may own certain rights in the present invention pursuant to NIH grant RO1-GM40676.

This application is a continuation of application Ser. No. 07/748,319, filed Aug. 21, 1991, now abandoned.

BACKGROUND OF THE INVENTION

1. Field of the Invention

The present invention is directed towards methods and compositions of amphiphathic compounds used as drugs to directly regulate G protein function in vivo. More particularly, the present invention is directed towards amphipathic compounds based on the key structural determinants of modified mastoparan and receptor-derived peptides. Such compounds would be used as novel drugs to combat a variety of disease states in which G proteins are intimately involved, e.g., asthma, gastric ulcers, cardiovascular disease, allergies, Parkinson's disease, small cell carcinoma of the lung, and the like.

2. Description of the Related Art

G proteins (guanine nucleotide binding regulatory proteins) are important to regulatory mechanisms operating in all human cells. Impairment of their function can perturb the cell's response to hormonal signals and adversely affect many intracellular metabolic pathways, thus contributing to the development and maintenance of a wide variety of disease states.

When functioning normally, G proteins act as an integral part of the signal transducing mechanism by which extracellular hormones and neurotransmitters convey their signals through the plasma membrane of the cell and thus elicit appropriate intracellular responses.

In its simplest terms, the signal transducing mechanism can be said to comprise three distinct components. A receptor protein with an extracellular binding site specific for a given agonist, such as the β-adrenergic receptor; a membrane-bound effector protein that when activated catalyzes the formation or facilitates the transport of an intracellular second messenger, an example is adenylate cyclase which produces cyclic AMP (cAMP); and a third protein which functions as a communicator between these two. G proteins fulfill this vital role as communicator in the generation of intracellular responses to extracellular hormones and agonists.

G proteins are composed of three polypeptide subunits, namely Gα, Gβ and Gγ. The conformation of each subunit and their degree of association changes during the signal transducing mechanism. These changes are associated with the hydrolysis of the nucleotide GTP to form GDP and $P_i$ (GTPase activity). The binding sites for GTP, GDP and the GTPase catalytic site reside in the α subunit.

The G protein cycle which occurs each time a signal is conveyed across the membrane can be summarized as follows:

In an unstimulated cell the G proteins are found in the resting state in which α, β and γ are complexed together and GDP is bound to Gα. The binding of an appropriate hormone or agonist to the receptor changes its conformation and causes it to activate the G protein by displacing GDP and allowing GTP to bind. This is the rate-limiting step of the G protein cycle. When GTP is bound to Gα it may dissociate from βγ and is able to bind to, and activate, adenylate cyclase which releases cAMP into the cytoplasm. GTP is then hydrolysed to GDP and the cycle is complete.

The series of complex interactions has evolved to allow signal amplification, such that a single hormone-receptor complex can trigger the production of several hundred second messenger molecules, such as cAMP. cAMP is a potent second messenger that binds to and activates protein kinase A (PKA). PKA was first shown to play a role in glycogen metabolism and is now known to influence a variety of processes including transcription.

A further attribute inherent in this system is that it allows several different receptors to interact with a signal-generating enzyme. Some act in such a way to activate the enzyme and some to inhibit it. This involves distinct α subunits $G_{s\alpha}$ (stimulatory) and $G_{i\alpha}$ (inhibitory) that combine with the same βγ complex to form stimulatory or inhibitory G proteins. An example of a receptor that interacts with $G_i$ to lower the concentration of cAMP is the $\alpha_2$-adrenergic receptor. The integration of the signals from $G_s$ and $G_i$ is one of the ways in which the level of cAMP in the cell can be fine-tuned in response to several different extracellular agonists.

Although G proteins were first identified and characterized in relation to the adenylate cyclase system, as discussed above, it is now apparent that they are involved in many other aspects of cell signalling. In particular, certain G proteins act in the signal transducing pathways that activate phospholipase C. This is a key enzyme that catalyzes the hydrolysis of phosphatidylinositol 4,5-bisphosphate ($PIP_2$) to form diacylglycerol (DG) and inositol 1,4,5-triphosphate ($IP_3$). DG causes the activation of protein kinase C (PKC) which phosphorylates a certain sub-set of cellular proteins and modulates their activity. For example, PKC is important in controlling the intracellular pH and in the transcriptional activation of specific genes. $IP_3$ is a small water-soluble molecule that causes the release of $Ca^{2+}$ from intracellular stores where it has been sequestered. $CA^{2+}$ itself is a potent intracellular messenger that plays a vital role in several metabolic and homeostatic pathways.

As has been shown, the importance of G proteins to the well-being of the cell cannot be stressed too much. It is not therefore surprising that any modulation of G protein function can have catastrophic consequences. Such is the case in individuals who are genetically deficient in $G_s$, their decreased responses to many hormones cause impaired growth, mental retardation and severe metabolic abnormalities.

Cholera and pertussis toxins also exert their effects through G proteins. Cholera toxin catalyzes the irreversible modification of $G_{s\alpha}$, by ADP-ribosylation, which destroys its GTPase activity and locks it into an active state. The resulting prolonged elevation in cAMP levels within the intestinal epithelial cells causes a large efflux of $Na^+$ and water into the gut, which can prove to be fatal. Pertussis toxin, made by the bacterium that produces whooping cough, alters the $G_{i\alpha}$ protein in a similar manner and prevents the inhibition of adenylate cyclase, thus also raising cAMP levels.

Following the identification of G proteins as important elements in many pathological conditions, several attempts have been made to design effective treatment strategies. However, each particular method employed suffers from certain drawbacks.

Many drugs are currently directed towards the hormone receptors themselves, such as the β-adrenergic agents used in the treatment of asthma. The usefulness of this class of drugs is limited by the problems of receptor desensitization and down regulation. In the normal physiological state the amount of functional receptor on a cell's surface is not constant, but is modulated in response to the hormone level. Down regulation of receptors is a general response to a high level of circulating hormone or agonist. The reduction of functional cell surface receptors desensitizes the cell and higher concentrations of agonist do not elicit an appropriately higher response. Any therapeutic agent which involves binding to the receptor is therefore partly flawed by the reduction in the number of receptors which will subsequently occur. It is evident that a downward spiral can result in which ever increasing doses are required to obtain the same effect, and at each dose the number of effective receptors would decline further.

The present invention seeks to by-pass the problem of receptor down regulation by using novel compounds that directly regulate G protein function.

Mastoparan (MP) is a peptide toxin from wasp venom that has been shown to directly stimulate G protein activation. MP is the prototype of a family of peptide toxins, collectively known as mastoparans, that form amphiphilic α helices. MP has been shown to stimulate guanine nucleotide exchange by G proteins in a manner similar to that of G protein-coupled receptors.

When MP is bound to a phospholipid bilayer, it forms an α helix that lies parallel to the plane of the membrane, with its hydrophobic face within the bilayer and its four positive charges (3 lysyl residues and terminal amino group) facing outward. G protein-coupled receptors are also believed to display clusters of positive charge near the inner surface of the membrane, some of which are predicted to form amphiphilic helices.

These observations gave rise to the idea that mastoparans could be used to directly regulate G protein function in vivo, and so form the basis of a novel family of drugs that would not suffer from the drawbacks of receptor desensitization. Such G protein-targeted drugs could also be used in cases where G protein mediated responses are important but in which no manipulatable receptor input is available.

This invention relates to the development of the above idea and the intelligent modification of MP to engineer features providing the optimum activity and desired G protein specificity.

SUMMARY OF THE INVENTION

The present invention addresses these and other shortcomings and disadvantages in the prior art by providing novel peptides that may be employed to activate one or more G proteins. It is proposed that the peptides of the invention will find a variety of pharmaceutical applications due to their action as G protein activators. Numerous bodily actions, as noted above, are mediated by G protein action. Thus, the inventors propose that the G protein activator peptides of the present invention may be employed to treat asthma, such as in aerosol formulations, as nasal decongestants due to their $\alpha_1$-adrenergic agonistic action, and even potentially as H1 or H2 blockers.

In one aspect of the present invention, peptides have been developed through modification of the mastoparan sequence to identify those modifications that will either enhance the G protein-stimulatory activity of the mastoparan sequence, or improve its selectivity for one or more G proteins. It is a particular object of the invention to provide analogs that are capable of selectively stimulating the $G_s$ protein in that this G protein is particularly involved in many β-adrenergic actions. However, it is clearly also an object of the present invention to provide peptide analogs that will have more selective actions against one or more of the other G proteins relative to mastoparan itself, such as $G_t$, $G_z$, $G_q$, $G_h$, $G_i$, and/or $G_{11}$. In any event, it is found that each of the G proteins tend to have a particular role in the modulation of cellular functions, and appear to be associated in many cases with peripheral nervous system action.

In particular embodiments relating to mastoparan analogues, therefore, the invention relates to peptides other than the naturally occurring mastoparans, MP, MP-A and MP-T (which have sequences of INLKALAALAKKIL (seq id no:66), IKWKAILDAVKKVL (seq id no:67), and INLKAIAAFAKKLL (seq id no:68), respectively). In general, the mastoparan analogues of the present invention are defined as comprising from about 12 to about 26 amino acids in length, that have incorporated one or more of the various modifications proposed by the inventors and found to result in a useful analogue. In this aspect, the peptides will within their structure comprise a mastoparan analog nucleus region having the following general formula:

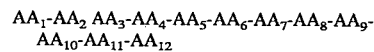

$AA_1$-$AA_2$ $AA_3$-$AA_4$-$AA_5$-$AA_6$-$AA_7$-$AA_8$-$AA_9$-$AA_{10}$-$AA_{11}$-$AA_{12}$ (Seq id no. 70)

wherein:

$AA_1$=L, W, A, F, or Y;

$AA_2$=K, A, R or Q;

$AA_3$=A or K;

$AA_4$=L, W, I, A, K or F;

$AA_5$=A, L, K, C or R;

$AA_6$=A, D or K;

$AA_7$=L, C, W, A, F or K;

$AA_8$=A, V, K or R;

$AA_9$=K, R, Q or A;

$AA_{10}$=K, A, R or N;

$AA_{11}$=L, I, W, V, A or K; and $AA_{12}$=L, A or C; or

Although naturally occurring MP, MP-A and MP-T each have 14 amino acids in their structures, the inventors have discovered that G protein modulating peptides may be longer or shorter than this, so long as the MP analogue peptides include the 12 amino acid nucleus discussed above. It will be appreciated that the foregoing general structure may be aligned with the MP, MP-A, and MP-T structures by comparing $AA_1$ with the third MP amino acid from the amino terminus, $AA_2$ with the fourth MP amino acid, and so on. However, in more preferred embodiments, the peptides of the present invention will comprise a 14 amino acid mastoparan analogue region within their structure, wherein the mastoparan analog region has the following structure:

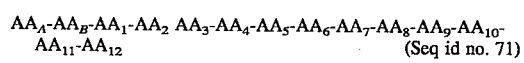

$AA_A$-$AA_B$-$AA_1$-$AA_2$ $AA_3$-$AA_4$-$AA_5$-$AA_6$-$AA_7$-$AA_8$-$AA_9$-$AA_{10}$-$AA_{11}$-$AA_{12}$ (Seq id no. 71)

wherein:

$AA_A$=I or C;

$AA_B$=N, K, Q or L;

$AA_1$=L, W, A, F or Y;

$AA_2$=K, A, R or Q;

$AA_3$=A or K;

$AA_4$=L, W, I, A, K or F;

$AA_5$=A, L, K, C or R;
$AA_6$=A, D or K;
$AA_7$=L, C. W, A, F or K;
$AA_8$=A, V, K or R;
$AA_9$=K, R, Q or A;
$AA_{10}$=K, A, R or N;
$AA_{11}$=L, I, W, V, A or K; and
$AA_{12}$=L, A or C.

A large number of peptides bearing a mastoparan analogue region, and falling within the foregoing general structure, have been synthesized, tested and shown by the inventors to have G protein modulatory activity. These peptides include the following (seq id no:1 through seq id no:47, respectively). INLKALAALAKKLL, INLKALAALAKKLA, INLKALAALAKKAL, INLKALAALAKKKL, INLKALAALAKALL, INLKALAALAKRLL, INLKALAALAAKLL, INLKALAALARKLL, INLKALAALKKKLL, INLKALAAAKKLL, INLKALAAKAKKLL, INLKALAKLAKKLL, INLKALKALAKKLL, INLKAAAALAKKLL, INLKAKAALAKKLL, INLKKLAALAKKLL, INLAALAALAKKLL, INLRALAALAKKLL, INAKALAALAKKLL, INFKALAALAKKLL, INLKAFAALAKKLL, INLKALAALAKALL, INLKALAALARALL, INLKALAALAQALL, INLAALAALAKALL, INLKALAALAAALL, INLRALAALAKALL, INLRALAALARALL, INLQALAALAKALL, INLQALAALAQALL, INLKALKALAKALL, INLQALKALAKALL, IQLKALAALAKALL, INYKALAALAKKIL, INYKALAACAKKIL, INYKALCALAKKIL, CNYKALAALAKALL, INYKALAALAKALC, INLKALAALAKNLL, ILLKALAALAKALL, INLRALRALARALL, INLKALAALKKALL, INWRAWRAWARAWL, INLRALAALRRRLL, INLKALAALKKKLL, CLLKALAALAKALL, LTAVLLTLLLYRINLKALAALAKALL. Numerous of these are shown to be particularly active and/or selective, as disclosed in more detail below (see, e.g., Table IV hereinbelow).

In still further embodiments, the present invention relates to peptides developed through a consideration of various receptor sequences found by the inventors to comprise useful G protein modulatory sequence regions. The receptors studied for this purpose include the turkey β-I3N, β-I2, β-I3C, β-I4N; the M1-I3N; Ha-α1-I3N; Ha-β2-I3N; M1-I2; M2-I3N; and the cow A1-I3N. From these studies, the following peptides were identified to comprise G protein modulatory regions, and can thus be employed in the construction of shorter or longer peptides as G protein modulators in accordance with the invention: CVYREAKEQIRKIDRVL; CVYREAKEQIRKIL; IVYREAKEQIRKIDRVL; IVYREAKEQIRKIL; CIYRETENRARELAALQGSET; CIYRETENRARELAALQGSETIL; CVYIVAKRTTKNLEAGVMKEIL; CVYIVAKRTTKNLEIL; Acetyl-CVFQVAKRQLQKIDKVL; CPLSYRAKRTPRRAALM; CPFRYQSLMTRARAKVI; REHKALKTLGIIC; CRSPDFRKAFKRLLC; CVYREAKEQIRKIDR; CISRASKSRIKKDKKEPVAIL; CISRASKSRIKKDKKIL; CVYVVAKRESRGLKSGLKTDIL; or CVYVVAKRESRGLKIL (seq id no:48 through seq id no:65, respectively).

Still further embodiments of the present invention reflect the inventors' discovery that the presence of relatively hydrophobic amino acids at the amino terminus of the selected peptide will provide an enhancement of G protein stimulatory activity. Preferred hydrophobic terminal amino acids include isoleucine, leucine and valine. However, it is proposed that other hydrophobic amino acids such as phenylalanine, tryptophan or methionine can be employed as well.

The inventors have also determined that particular advantages in terms of pharmacologic efficacy will be realized where the peptide has been modified at one or more of its termini to "protect" the peptide against degradation and thereby enhance it action. A convenient means of protecting the peptide is through amidation or esterification of its carboxy terminus or acylation of its amino terminus. Carboxy terminal amidation of peptides has generally been found to be required for obtaining activity. Therefore, prior to formulation for administration to patients, one will desire to provide the peptide in amidated form. The effects of amino terminal acetylation are more variable. It is more preferrable to add larger alkyl groups to the amino terminus, such as by attachment to a cysteine residue using n-iodoalkanes. The inventors have found that alkylation of such a cysteine residue employing, e.g., C12 or C16, results in a significant increase in potency of both the mastoparan-based activating peptides, as well as the receptor-based peptides, discussed above. While preferred embodiments employ C12 or C16, the present invention contemplates that the certain benefits may be achieved through alkylation of the amino terminus with any convenient hydrophobic alkyl group, such as C10–C22, C12–C18, etc. The reason for this enhancement of potency is not clear, but could be due to enhanced binding to the membrane surface and resultant stabilization of an amphipathic structure which may not be fixed when the peptide is in aqueous solution.

The inventors have also determined that an enhanced hydrophobicity of the C-terminus tends to have beneficial effects as well. An exemplary approach to enhancing the hydrophobicity of the C-terminus is through the addition of short hydrophobic peptide regions, such as a hydrophobic dipeptide region. As mentioned above, exemplary hydrophobic amino acids which may be added to the C-terminus include isoleucine, leucine and valine. However, the invention is certainly not limited to these hydrophobic amino acids.

In still further embodiments, the present invention concerns peptides that incorporate one or more D-isomers of amino acids. D-isomers are generally less susceptible to biological degradation, and therefore should exhibit an increased half life in the body. The inventors have found that peptides constructed using D-isomers of amino acids nevertheless exhibit G protein modulatory activity, and therefore can be employed in connection with the present invention.

The inventors have further determined that various general structural changes in the basic mastoparan structure can be employed to enhance G protein stimulatory activity. For example, the replacement of the lysine at position 12 yields a dramatically increased activity as an activator of $G_i$ and $G_o$. In fact, increases in activity can be greater than 10-fold by the replacement of lysine at position 12 with alanine. From this general observation, the inventors have found that the replacement of $AA_2$, $AA_9$ or $AA_{10}$ (corresponding to positions 4, 11 and 12 of mastoparan, respectively) with amino acids such as alanine, glutamine or arginine can result in peptides having an improved pharmacology. Furthermore, the inventors have found that where at least two of these residues comprise an alanine, glutamine or arginine, then particular advantages are achieved, generally in terms of enhanced potency and maximal effect.

Of course, in that the peptides of the present invention are intended for administration to mammals, particularly humans, the present invention concerns embodiments in the preparation of pharmacologic compositions which comprise a therapeutically effective amount of one of the foregoing described G protein modulatory peptides, dispersed in a pharmacologically acceptable carrier or diluent. Since the peptides of the present invention will find their greatest utility through topical administration, such as in the treatment of asthma, ulcers, glaucoma, respiratory tract congestion or inflammation, and the like, pharmaceutical compositions of the present invention will preferably employ a carrier that is adapted for topical administration. For ophthalmic applications, one would desire to employ a sterile solution. In any event, pharmaceutical compositions of the present invention will generally include acceptable salts and/or buffers for maintaining a selected pH, such as between about 6 and 8, and more more preferably between about 7 and 7.5. For administration as inhalants, such as in the treatment of asthma, one may also desire to formulate the composition in a manner to allow its administration in the form of an aerosol.

As a further matter, it is pointed out that the inventors propose that the peptides of the present invention will find additional application as structural models for computer-based analysis leading to the design of non-peptidyl agents that will mimic the effect of these peptides.

DETAILED DESCRIPTION OF THE PREFERRED EMBODIMENTS

Introduction

Figure 1:
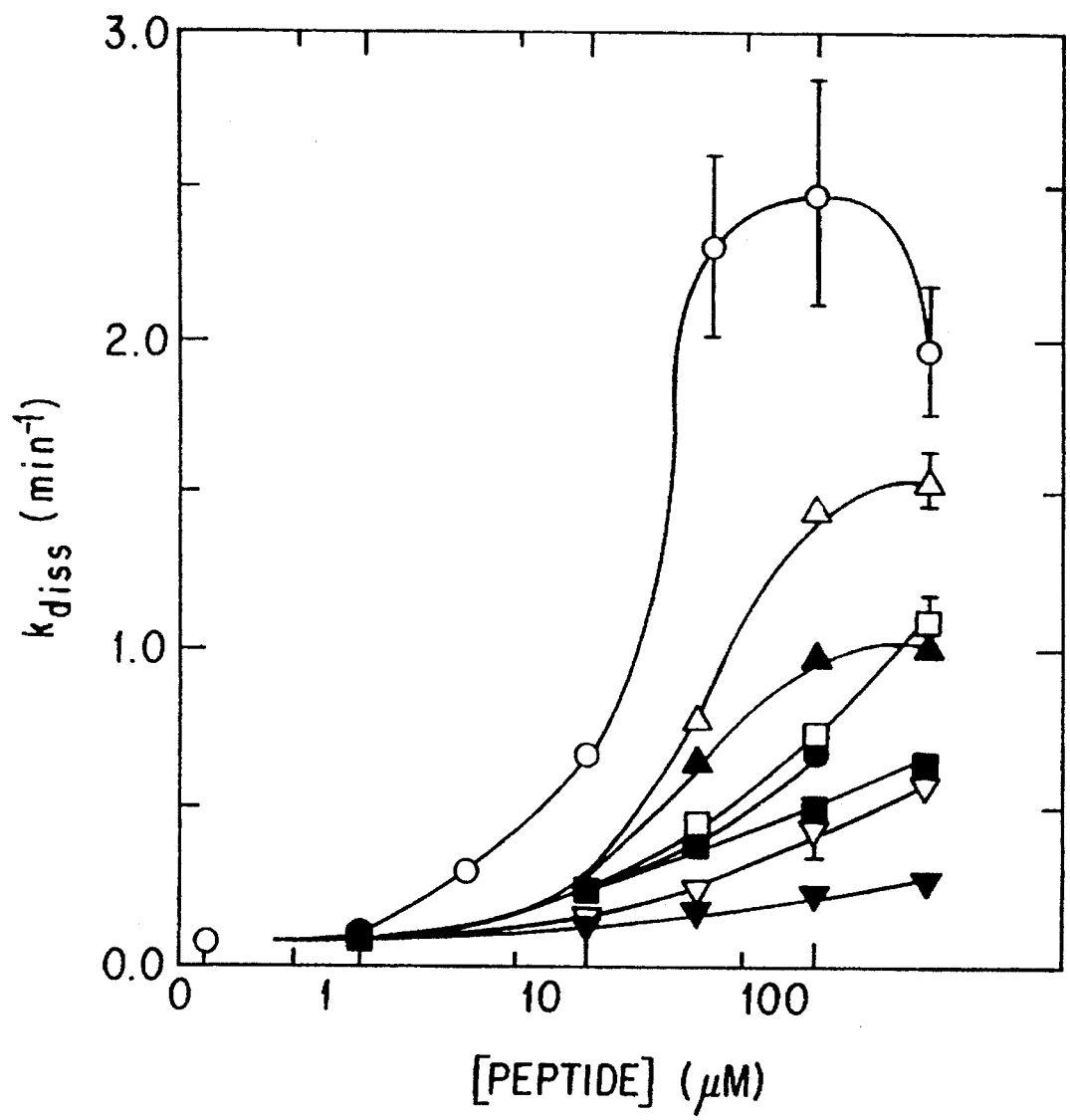
FIG. 1. Stimulation of GDP/GTP exchange by analogs of MP. The release of [$\alpha$-$^{32}$P]GDP from $G_i$ was measured at 30° C. in the presence of the concentrations of several different MP analogs whose structures are listed in Table I: O, Mas7; $\Delta$, Mas8; ▲ Mas9; □, Mas19; ●, MP; ■, MP-X; ▽, MAS14; ▼, Mas6. First order dissociation rate constants ($k_{diss}$) were determined from duplicate four-point time courses as described under "Experimental Procedures."

G proteins are important to regulation in all human cells and their function is involved in a wide variety of disease processes. Signaling through G proteins is usually initiated by receptors for hormones, neurotransmitters and other signaling molecules. Higashijima and co-workers (Higashijima et al., 1987) first suggested that mastoparan, a peptide toxin from wasp venom, directly stimulates G protein activation. This suggestion was confirmed in 1988 (Higashijima et al., 1988) and further data indicated that mastoparans stimulate G protein activation through a mechanism very similar to that used by receptors (Higashijima et al., 1990). Mastoparan is the prototype of a family of about 10 peptide toxins isolated from related wasps (known collectively as mastoparans). The present inventors have since synthesized and tested numerous peptides that are amphipathic and cationic and can promote G protein activation. These peptides have been synthesized based on a consideration of mastoparan structure, as well as the structure of various G-protein-linked receptors such as several isoforms of α1, α2, β-adrenergic, muscarinic 1 and 2 and dopamine D1 receptors. The peptides of the present invention, which are based on mastoparan and receptor sequences, are generally considered to be activator peptides in that they activate the action of one or more G proteins.

At the core of the present invention, therefore, is the finding that amphipathic compounds can be used as drugs to directly regulate G protein function, thereby manipulating disease states in which G proteins are significant. G proteins are diverse and are intimately involved in numerous diseases (asthma, ulcers, many cardiovascular diseases, Parkinson's disease) and are at least peripherally involved in most physiological regulatory processes. Furthermore, these amphipathic compounds can either activate G proteins or block their activation by receptors.

The present invention relates in part to the ability of mastoparans and receptor peptides to regulate G proteins directly. This can allow the development of drugs to treat diseases either by promoting the activation of specific G proteins or by blocking their activation by receptors. Because the mastoparans and congeners can fulfill these functions, the inventors propose that these agents will prove useful as a new class of therapeutically useful drugs. Activator peptides of the present invention are highly efficacious: peptides of the present invention can frequently achieve in vitro stimulation of G protein activation far greater than that caused by receptors. The use of these peptides would largely obviate receptor desensitization and down-regulation, which frequently limit the utility of receptor-directed drugs. G protein-targeted drugs could also be used in cases where G protein mediated responses are important but in which no manipulatable receptor input is available.

Furthermore, the use of G protein-targeted drugs forgoes the exquisite selectivity of receptor-directed drugs. This might initially limit the use of the compounds to topical or local applications because of potentially untoward effects of stimulating G protein functions in non-target tissues. Moreover, the susceptibility of peptides to hydrolysis by cellular and serum peptidases and proteases could serve to compromise the duration of action of the present activator peptides. However, in that the inventors have found that stable all-D-isomers of mastoparan are also active, such agents can likely be employed to circumvent problems of hydrolysis and susceptibility to enzymatic degradation in that most enzymes are specific of L-isomeric substrates.

Specific Applications

To be an effective drug, an activator peptide must be adequately specific for the G protein to be regulated. The mastoparans themselves show some specificity. For example, mastoparan is most effective as an activator of $G_o$, $G_z$ and $G_i$. In the inventors' initial screen of systematically modified mastoparan congeners it was found that many changes in the mastoparan structure slightly changed the selectivity of mastoparan between $G_i$ and $G_o$ by less than 5-fold. Such modifications included, e.g., those represented by analogs Mas4, Mas5, Mas11, Mas16, and Mas17 (see Table IV). However, several of these compounds also had significant effects on $G_s$, including ER21 and ER30 (see Tables V and VI).

A variety of applications are proposed for the G protein activator peptides of the present invention. For example, due to their β-adrenergic activity, a $G_s$-directed activator peptide could be used as an aerosol bronchodilator to treat asthma. A number of peptides set forth below (see Tables IV and V) have significant $G_s$-specific action. Examples include C12-ER18, C12-ER19, ER36 and even ER40 (Table V). Asthma is a widespread disease that is not treated adequately by β-adrenergic drugs (that ultimately work via $G_s$). Topical application seems particularly appropriate for asthma treatment, and is currently used for other anti-asthma drugs. Potency should not generally be a problem because of the route of application. Intense pharmacologic intervention during the initial spasmic phase of asthma is particularly valuable because limitation of initial spasm seems to delay or diminish the delayed inflammatory asthmatic response.

The peptides of the invention should also find application as nasal decongestants, which are generally $\alpha_1$-adrenergic agonists. The $\alpha_1$-adrenergic agonists promote activation of $G_q$ and/or $G_{11}$ (or, perhaps, a newly identified G protein known as $G_h$). Direct activation of these proteins might have the advantages discussed above for bronchodilators. Furthermore, β-adrenergic antagonists and muscarinic agonists are widely used in the treatment of glaucoma, although their effectiveness is limited. It is proposed that the peptides of the present invention will be applicable to the treatment of glaucoma, such as when formulated into an ophthalmic dosage form for topical application. For example, a peptide that activates $G_q$ would be a far more active agent than the muscarinic agonists, to which tolerance develops rapidly. A peptide that blocks the activation of $G_s$ might do far better than the currently used β-adrenergic antagonists.

Both H1 and H2 anti-histamines are currently of great therapeutic importance: H1 blockers to treat nasal allergic reactions and H2 blockers to treat gastric ulcers. These receptors work on G proteins that have not been unambiguously identified. However, these diseases present readily accessible sites for topical application and do not require dissemination throughout the body.

Surprisingly, small cell carcinoma of the lung is best treated (although not well) by methadone, a selective opiate agonist. Although this is clearly a somewhat speculative application, stimulation of the signaling pathway in these cells might add to the pharmacologic treatment of these tumors.

Structural Determinants of the Function of Activating Peptides

Mastoparan-Based Peptides

The inventors have synthesized and tested a large number of peptides for their ability to activate G proteins or to block activation. From these studies, a number of trends in terms of the structure-activity relationship (SAR) of such peptides have been observed. For example, in referring to the natural mastoparan sequence, the inventors have found that lysine 4 and lysine 11 may be replaced by glutamine, arginine, or alanine with little if any negative effect and, in some cases, slight positive effect. However, replacement of lysine 12 by alanine yields dramatically increased activity as an activator of $G_i$ and $G_o$. A number of studies have been carried out by the inventors to confirm the generality of this observation. In fact, increases in activity can be $\geq 10$-fold when tested at suitable concentrations and in suitable media. For this reason, mastoparan congeners having an alanine at the position 12 are particularly preferred.

The inventors have also found that the addition of a lysine residue at position 10 has little effect on the activity of mastoparan but greatly diminishes its lytic capacity, in some cases by more than 100-fold. This is extremely important in decreasing toxic, irritant and inflammatory properties of mastoparan-based peptides. Thus, lysine 10, alanine 12 mastoparan is the most effective and least toxic $G_o$ activator available.

A variety of structure modifications have been studied by the inventors to determine which, if any, have a significant pharmacologic effect. It has somewhat surprisingly been found that carboxy-terminal amidation of mastoparans is required for activity. The reason for this is unclear but could be due to the need for a hydrophobic carboxy terminus. However, the effects of amino terminal acetylation are somewhat more variable. For peptides that activate $G_i$ and $G_o$, acetylation decreases activity by 50–70%. Little effect of acetylation has been observed for the peptides that activate $G_s$.

While the pharmacologic effect of amino terminal acetylation tends to be somewhat variable from peptide to peptide, the inventors have found that alkylation of the amino terminus with higher alkyls, such as C12 to C16, can have a dramatic effect. Numerous means of amino terminal alkylation are known in the art, and it is proposed that virtually any such means as are known in the art may be employed in connection with the invention and obtain the advantages of the invention. The inventors have rountinely employed the addition of a cysteine residue, in that amino acids such as cysteine may be alkylated readily. Moreover, the addition of a cysteine residue at position 1 has little effect on activity in the presence of a sulfhydryl compounds. Thus, the addition of such a cysteine residue is preferred where amino terminal alkylation is contemplated in that the cysteine provides a ready substrate for alkylation. Alkylation (C12, C16) of this cysteine residue using n-iodoalkanes increased the potency of mastoparan-based activating peptides as well as the receptor-based peptides as well.

Studies of mastoparan analogues in which more than one lysine residue is converted to alanine, glutamine or arginine indicates that two positive charges (amino terminus and one lysine) seem to be mandatory for high activity and that three is generally better. Replacement of lysine 4 with lysine at the 7 position (which should also be on the hydrophilic face of the helix) is generally without significant effect.

It has been shown by others that several novel synthetic substance P antagonists can block the ability of mastoparans to promote the activation of $G_o$ and $G_i$ mediated events. They can also block stimulation in a reconstituted system initiated by the M2 muscarinic cholinergic receptor. Partial agonist activity of these peptides is observed if they contain positive charge, but a pentapeptide that contain D-tryptophan residues is a full antagonist. This antagonist is effective on $G_o$ and $G_i$. It is also effective on $G_s$, although this interaction is not yet well characterized.

Receptor-Based Peptides

The inventors have made a major effort to develop peptides that activate $G_s$, the G protein that stimulates adenyl cyclase. Among the mastoparan analogues synthesized so far, only leucine-2, alanine-12 activates $G_s$ well ($\geq$10-fold). Others stimulate by less than 4-fold. In an attempt to identify more highly $G_s$ active peptides, the inventors have synthesized several amphipathic peptides having a sequence designed based on a consideration of the third intracellular loop of various receptors. It has been postulated that the third intracellular loop is important for specifying a receptor's specificity and selectivity among G proteins (Wong et al., 1990, and the inventors' unpublished observations). Thus, a number of peptides of peptides have been synthesized and tested, and found to have significant action.

The unmodified receptor-based peptides, with or without carboxy terminal hydrophobic dipeptide extensions, were functionally inactive or only weakly active. When a cysteine residue was added at the amino terminus, and the sulfhydryl group alkylated, these peptides became potent and effective activators of $G_s$. They are among the most highly selective peptide activators that we have yet synthesized because they are only weakly active against $G_o$, $G_i$, $G_z$, and $G_q$. Several activate $G_s$ more than 20-fold. These are the peptides what are proposed for use as either anti-asthma drugs or as the structural precursors for developing non-peptide anti-asthma drugs.

Required structural determinants for the receptor-based peptides so far are known to include a C-terminal hydrophobic dipeptide extension and amino terminal alkylation (C12 appears optimal). The inventors have not systematically modified the internal sequences of the receptor-based peptides as they have for the mastoparan-based peptides, to further optimize activity, selectivity, or potency. The preferred receptor-based peptide is based on the sequence of the turkey erythrocyte β-adrenergic receptor (e.g., peptides C12-ER18, C12-ER19, C12-ER22, C12-ER23. C12-ER36).

The dependence of a peptide's regulator activity on its ability to form α-helices when binding to micelles or bilayers should be stressed. This ability can be determined from circular dichroic spectra of the candidate peptide in the presence and absence of lipid (Higashijima et al., 1990). This is of general diagnostic importance, as indicated by more recent studies of the $G_s$-directed β-adrenergic receptor-based peptides carried out by the inventors. The peptides that have not been acylated, and are thus inactive display CD spectra characteristic of random coil both in aqueous solution and in the presence of phospholipid vesicles. Active (acylated) peptides give distinct α-helical CD spectra only in the presence of bilayers, but not in aqueous solution. The inventors propose that distinct changes in CD spectrum caused by the addition of phospholipid is a good first test for the ability of a peptide to form an amphipathic structure when bound to a membrane and to present its charged face to the aqueous environment.

Peptide Preparation

The conditions for preparation, alkylation and purification of peptides of the present invention is well within the skill of the art when considered in light of the present invention. For peptide synthesis, the inventors employ standard peptide synthesis technology (e.g., using a solid phase peptide synthesizer), and the peptides may be readily purified by reverse-phase HPLC. The inventors routinely react the cysteine containing peptide with about two mole equivalents of the correct iodoalkane in a slightly basic aqueous solution with a small amount of DTT. The addition of DTT has been found to increase the yield from about 30% to about 90%. In a typical protocol, the inventors employ approximately 1 μmol Cys-containing peptide, 2 μmol iodododecane (or other iodoalkyl), 10 μmol DTT, 30 μmol base ($KHCO_3$), in 550 μl DMF and 150 μl $H_2O$. The reaction can be completed in 1 minute at 110°.

Therapy and Pharmaceutical Compositions

For the treatment of the various disorders where one desires to modulate G protein function, it will generally be desireable to employ a dosage form and amount that will be adequate to effect modulation of the selected G protein, without effecting appreciable effect on G proteins that are not associated with the targeted disorder or in non-target tissues that may contain the G protein target. Generally speaking, where a topical or parenteral application is envisioned, one will desire to administer a dosage that will deliver an amount that will achieve an intracellular concentration of approximately 1 to 10 μM, as outlined in Example 2. Studies by the inventors using intact cells indicate that similar concentrations in extracellular medium are efficacious. For a typical application as injectibles, aerosols, drops, creams, etc., the actual concentration will generally be adjusted to achieve this local concentration.

The novel peptides of the invention are quite stable and may be administered alone or in combination with pharmaceutically acceptable carriers, in either single or multiple doses. Suitable pharmaceutical carriers include diluents, sterile aqueous solutions, and the like. Peptides of the present invention may not only be advantageously employed for the preparation of parenteral, topical and/or aerosol pharmaceutical compositions for administration as described above, but more particularly for the preparation of pharmaceutical compositions suitable for use as ophthalmic solutions. Such ophthalmic solutions are of principal interest for the treatment of ophthalmic disorders such as glaucoma by topical administration and the treatment of such conditions in this manner is a preferred embodiment of the present invention. Thus, for the treatment of glaucoma the compounds of this invention are administered to the eye of the subject in need of treatment in the form of an ophthalmic preparation prepared in accordance with conventional pharmaceutical practice, see for example "Remington's Pharmaceutical Sciences" 15 Edition, pages 1488 to 1501 (Mack Publishing Co., Easton, Pa.).

Typical ophthalmic preparations will contain a selected peptide or a pharmaceutically acceptable salt thereof in a concentration that will conveniently achieve a local concentration of about 1 to about 10 µM. Thus, it is proposed that preparations of from about 0.001 to about 0.1% by weight, preferably from about 0.0015% in a pharmaceutically acceptable solution, suspension or ointment, will find utility. Some variation in concentration will necessarily occur, depending on the particular compound employed, the condition of the subject to be treated and the like, and the person responsible for treatment will determine the most suitable concentration for the individual subject.

Ophthalmic preparations will preferably be in the form of a sterile aqueous solution containing, if desired, additional ingredient, for example preservatives, buffers, tonicity agents, antioxidants and stabilizers, nonionic wetting or clarifying agents, viscosity-increasing agents and the like. Suitable preservatives include chlorobutanol, thimerosal and the like.

Therapeutic compositions of the present invention will generally include suitable buffers include boric acid, sodium and potassium bicarbonate, sodium and potassium borate, sodium and potassium carbonate, sodium acetate, sodium biphosphate and the like, in amounts sufficient to maintain the pH at between about 6 and 8, preferably between about 7 and 7.5. Suitable tonicity agents are dextran 40, dextran 70, dextrose, glycerin, potassium chloride, propylene glycol, sodium chloride, and the like, such that the sodium chloride equivalent of the solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol.

Where desired, compositions may include suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. Ophthalmic preparations will be administered topically to the eye of the subject in need of treatment by conventional methods, for example in the form of drops or by bathing the eye in the ophthalmic solution.

The following examples illustrate preferred embodiments of the present invention in terms of laboratory practices found by the present inventors to work well in the practice of the invention. However, in light of this disclosure, those of skill in the art will appreciate that numerous alternatives may be employed without departing from the spirit and scope of the invention. Therefore, the present invention is not intended to be limited to the specific methodology set forth hereinbelow.

EXAMPLE 1

Regulation of $G_i$ and $G_o$ by Mastoparan, Related Amphiphilic Peptides, and Hydrophobic Amines Mechanism and Structural Determinants of Activity This example relates to the interaction with, and regulation of, G proteins by amphiphilic peptides. The development of reproducible assay conditions for in vitro measurement of peptide-stimulated nucleotide exchange has enabled this interaction to be analyzed in detail. Using this methodology it has been determined that mastoparan (MP) stimulates guanine nucleotide exchange by G proteins in a manner similar to that of G protein-coupled receptors. This stimulation involves 1) MP stimulated exchange by isolated G protein α subunits and αβγ trimers. Relative stimulation was greater with αβγ trimers and βγ subunits could increase net MP-stimulated activity. 2) MP action was enhanced by reconstitution of trimeric G protein into phospholipid vesicles, with the membrane-bound α-helical conformation of MP appearing to be the activating species. 3) MP blocked the ability to $G_o$ to increase the affinity of muscarinic receptors for agonist ligands, suggesting that MP and the receptor may compete for a common binding site on $G_o$. 4) MP stimulated steady state GTPase activity at <1 µM $Mg^{2+}$ and stimulated the dissociation of both GDP and guanosine 5'-0-(3-thiotriphosphate) at <1 nM $Mg^{2+}$. Millimolar $Mg^{2+}$ blocked the stimulatory effect of MP. This is in keeping with the knowledge that both high and low affinity $Mg^{2+}$ binding sites are on the α subunit.

The details of the mechanistic studies are not believed to be of particular importance to an overall understanding of the present invention, but are nonetheless incorporated herein by reference (Higashijima et al., *J. Biol. Chem.*, 265(24):14176–14186, 1990).

This example in particular relates to the structure-activity relationships for the regulation of $G_i$ and $G_o$ by MP, several related and unrelated biological peptides, and a series of synthetic peptides designed to test the importance of individual structural aspects of the MP molecule.

EXPERIMENTAL PROCEDURES

Materials

MP was synthesized and purified as described by Saito and his colleagues (*Chem. Pharm. Bull.*, 32:2187–2193, 1984, incorporated herein by reference). The MP analogs listed in Table I were synthesized by standard solid phase methods and purified by C-4 HPLC using an acetonitrile gradient in 0.1% trifluoroacetic acid. Analytical C-4 HPLC monitored at 220 nm showed less than 2% impurity in all samples. The identity of the peptides was monitored by 400-MHz or 250-Mhz $^1$H NMR spectroscopy for MP and MP-X and by mass spectroscopy for the other analogs. *Saacharomyces cerevisiae* α-mating factor, calcitonin, and [D-Ala$^2$]Leu-enkephalin were prepared at the Peptide Institute (Osaka) and gramicidin S, glucagon, and compound 48/80 were purchased from Sigma. BAC was purchased from Sigma, and other alkylammonium compounds were from Aldrich. The critical micelle concentration of BAC was measured in the buffer used for GTPase assays (see below) using 1,6-diphenyl-1,3,5-hexatriene according to the method of Schrock and Gennis, (*J. Biol. Chem*, 252:5990–5995, 1977, incorporated herein by reference). The critical micelle concentration was approximately 20 µM.

[$\gamma$-$^{32}$P]GTP, [$\alpha$-$^{32}$P]GTP, and [$^{35}$S]GTP$\gamma$S were purchased from DuPont-New England Nuclear. All lipids were purchased from Avanti Polar Lipids, and other reagents are from standard sources.

Protein Purification $G_o$ was purified from bovine brain in the form of resolved $G_o\alpha$ and $\beta\gamma$ subunits as described by Higashijima, et al., 1987, (incorporated herein by reference), which were mixed before each experiment at a 0.5 molar ratio ($\alpha$:$\beta\gamma$). Briefly, proteins were extracted from bovine cerebral cortical membranes and chromatographed on DEAE-Sephacel (Pharmacia LKB Biotechnology Inc.) according to Sternweis and Robishaw, 1984, (incorporated herein by reference), except that the column buffer contained AMF to allow separation of $\alpha_o$ and $\beta\gamma$. Each pool was chromatographed on Ultrogel AcA34 (LKB) in the presence of AMF, diluted 4-fold in 20 mM Tris-Cl, pH 8.0, 1 mM EDTA, 1 mM dithiothreitol, AMF, and applied to a 100-ml column of heptylamine-Sepharose that was equilibrated in the same buffer that also contained 25 mM NaCl and 0.25% cholate. After the column was washed in the same buffer that contained cholate and 100 mM NaCl, G proteins were eluted with a 600-ml gradient from 100 mM NaCl plus 0.25% cholate to 50 mM NaCl plus 1.3% cholate. Heptylamine-Sepharose removed subunits from the $\beta\gamma$ subunits and helped remove $\alpha_i$ from $\alpha_o$.

Purification of $\alpha_o$ and $\beta\gamma$ was completed by chromatography on DEAE-Sephacel that was eluted with a gradient of 0–250 mM NaCl in the presence of 0.6% Lubrol and AMF. AMF was removed by chromatography on hydroxyapatite and Sephadex G-25 as described by Sternweis, et al., 1981, incorporated herein by reference. $G_i$ was purified as the $\alpha\beta\gamma$ trimer from rabbit liver as reported by Bokoch, et al., 1984, incorporated herein by reference. The $G_i$ used in this study could be recognized on a Western blot by anti-$G_i$-1 and anti-$G_i$-3 antibodies but not by anti-$G_i$-2 antibody, as documented by Mumby, et al., 1983, incorporated herein by reference. Purified recombinant $\alpha i,1$ was synthesized in *E. coli* prepared to the specifications of Linder, incorporated herein by reference. During purification, G protein $\alpha$ subunits were assayed by [$^{35}$S] GTP$\gamma$S binding according to the method of Higashijima, 1987, incorporated herein by reference). By subunits were assayed according to their ability to deactivate Gs, as detailed by Northup, 1983, incorporated herein by reference.

G proteins were reconstituted into phospholipid vesicles composed of dioleoyl-PC/bovine brain PS/1-palmitoyl,2-oleoyl-PE (3:4:3) as reported previously by Higashijima et al., 1988, incorporated herein by reference.

Muscarinic cholinergic receptor was purified from porcine brain as described by Haga and Haga, 1985, incorporated herein by reference. To co-reconstitute receptors and $G_o$ into phospholipid vesicles, receptor (5 pmol), $G_o$ $\alpha$ subunit (100 pmol), and $\beta\gamma$ subunits (250 pmol) were mixed with 25 µg of a mixture of PE and PS (3:2, w:w) in 50 µl of 20 mM sodium Hepes, pH 8.0, 1 mM EDTA, 2 mM MgSO$_4$, 100 µM NaCl, 0.375 mg/ml deoxycholate, 0.075 mg/ml cholate and held at 0° C. for 30 min. Each protein was added in less than 0.2 volume of the detergent-containing solution in which it was purified, and the lipid was added as a sonicated dispersion in the reconstitution buffer. The mixture was chromatographed on AcA34 as described previously (Higashijima, et al., 1988) and vesicles were collected in the void volume. Recovery of activity in the vesicles was typically 40% for $G_o$ and 8% for receptor, as compared to the work of Haga, 1985; 1986, incorporated herein by reference.

Assays

Methods for the assay of steady state GTP hydrolysis and GTP$\gamma$S binding have been described previously by Higashijima, 1987, and Ferguson, 1986, and incorporated herein by reference. Unless noted otherwise, assays of steady state GTP hydrolysis and of the binding and dissociation of guanine nucleotides were carried out in the buffer described previously, but without detergent and with 1.1 mM MgSO$_4$ and the nucleotide specified in the text. When necessary, the concentration of free Mg$^{2+}$ was adjusted using EDTA buffers as described previously by Higashijima, 1987, and incorporated herein by reference.

The concentration of free Mg$^{2+}$ in assay medium that contains 5 mM EDTA and no added Mg$^{2+}$ is estimated to be 0.1–0.2 nM according to Brandt et al., 1988 and 1983. The latter Brandt article also discusses the use of molar turnover numbers, using GTP$\gamma$S binding activity to measure to concentration of total G protein.

To measure the MP-catalyzed dissociation of [$\alpha$-$^{32}$P]GDP or [$^{35}$S]-GTP$\gamma$S, labeled nucleotide was first bound to G protein (approximately 100 mol in 50 µl) by incubation of the Lubrol-solubilized G protein with a molar excess of nucleotide in assay buffer that contained 10 mM MgSO$_4$ and 0.1% Lubrol. Incubation was for 20 min at 20° C. (for $G_o$) or for 30 min at 30° C. (for $G_i$), In the case of [$\alpha$-$^{32}$P]GDP, EDTA was then added to 12 mM. Liganded G protein was reconstituted by mixing it with 10 µg of dioleoyl-PC/bovine brain PS/1-palmitoyl,2-oleoyl-PE (4:3:3) in 50 µl of 50 mM sodium Hepes (pH 8.0), 1 mM dithiothreitol, 0.1% Lubrol 12A9 plus either 12 mM EDTA and 10 mM MgSO$_4$ (for [$\alpha$-$^{32}$P]GDP) or 1 mM EDTA and 1.1 mM MgSo$_4$ (for [$^{35}$S]GTP$\gamma$S) and chromatographing the mixture on a 3-ml column of Ultrogel AcA34 in 50 mM sodium Hepes (pH 8.0), 1 mM EDTA, 1 mM dithiothreitol. The gel filtration during reconstitution removes unbound nucleotide. Dissociation was initiated at 30° C. for $G_i$ or 20° C. for $G_o$ by the addition of G protein-containing vesicles to assay medium that contained 1 µM unlabeled GDP, GTP, or GTP$\gamma$S and free Mg$^{2+}$ at 0.1 mM or other concentrations as shown in the figures. Dissociation was terminated by 5-fold dilution at 0° C. into buffer that contained 0.1% Lubrol and, in the case of GDP, AMF to stabilize binding. Bound nucleotide was determined by binding to nitrocellulose filters as described (Ferguson, 1986), and incorporated herein by reference. Dissociation of nucleotide displayed single component, first order kinetics. Data were analyzed using a nonlinear least squares fitting program.

The rate of hydrolysis of protein-bound [$\gamma^{32}$P]GTP was measured essentially as described previously (Higashijima, 1987) at 20° C. in assay medium that contained 2 ppm Lubrol 12A9. $G_o$ (10 nM) was incubated in assay medium for 16 min with 100 nM [$\gamma$-$^{32}$P]GTP to allow nucleotide to bind. Hydrolysis was initiated by the addition of 1.3 mM MgSO$_4$. Excess unlabeled GTP was also added such that only a single turnover was measured. The production of [$^{32}$P]P$_i$ was measured as described by Higashijima, 1987.

The competitive binding of [$^3$H]QNB and acetylcholine to reconstituted muscarinic cholinergic receptors was measured at 30° C. in 100 μl of 20 mM Tris-Cl, pH 8.0, 1 mM EDTA, 2 mM MgSO$_4$, 100 mM NaCl, 1 mM dithiothreitol, 0.1 mg/ml bovine serum albumin. After equilibration for 60 min, vesicles were collected and washed on Whatman GF/F glass fiber filters, as described previously, for the assay of the β-adrenergic receptor (Fleming & Ross, 1980), and incorporated herein by reference.

Non-specific binding of [$^3$H]-QNB, which was determined in the presence of 2 μM atropine, was not altered by MP or by guanine nucleotides.

Intrinsic tryptophan fluorescence was measured as described by Higashijima, 1987.

Circular Dichroism

CD spectra of peptides were measured using an Aviv model 60DS spectrometer at 25° C. in 1-mm pathlength cells. Spectra were scanned at 1 nm intervals for 3 s, and three scans were averaged. Peptides were dissolved at 20 μM in 5 mM Tris-Cl, pH 7.5, in the presence or absence of sonicated 1 mM 1-palmitoyl,2-oleoylphosphatidylcholine. Fractional helical content for each peptide was calculated according to the assumption that, for 100% helix and 14 peptide bonds, $\theta_{222}=36,000 (1-2.6/14)$.

RESULTS

Structure-Activity Relationships for MP Analogs

Several congeners of MP were synthesized in order to characterize the structural features that allow it to catalyze the activation of G proteins. They included both natural peptides that are found in the venoms of different wasps and nonbiological congeners that were designed to test the effects of net positive charge, the spacing and location of charge, and α-helical conformation on MP's regulatory activity. The structures of these peptides and their fractional α helical contents, hydrophobicities, and calculated hydrophobic moments are shown in Table I.

TABLE I

Structure of MP analogs

Analogs in each group displayed virtually identical regulatory activities in the GDP exchange assay shown in FIG. 1. Group VIII analogs were not evaluated in this assay but were slightly more active than group IX analogs in GTPase assays. The hydrophobic moment (μ), a measurement of the asymmetry with which hydrophobicity is distributed around the axis of a helix, was calculated according to Eisenberg et al. (1984) using the hydrophobicity values of Janin (1979) Average hydropathy (HΦ) was calculated using the values of Kyte and Doolittle (1982) without correction for free N-terminal amino groups. Fractional helical contents of some of the peptides were determined by circular dichroism (FIG. 2) in the presence or absence of 1 mM phospholipid using the methods and formula described under "Experimental Procedures." Analogs are numbered arbitrarily except for those noted with letters, which are found in wasp venoms. (Biological MP-A has an Ile at position 13.) Hyphens indicate identity with MP. The 17 peptides of this table represent seq id nos: 66, 5–8, 18, 17, 67–69, 12,1 13, 16, 9, 11, 4 and 15, respectively. Peptide INWKGIAAMAKKLL is represented by seq id no: 69.

| | | Structure | μ | HΦ | − PC | + PC % α Helix |
|---|---|---|---|---|---|---|
| I | MP | I NLKALAALAKKI L | 0.331 | 1.16 | 19 | 61 |
| II | Mas7 | - - - - - - - - - - - AL- | 0.273 | 1.51 | 26 | 69 |
| III | Mas8 | - - - - - - - - - - - RL- | 0.304 | 1.06 | 28 | 79 |
| IV | Mas9 | - - - - - - - - - - A- L- | 0.227 | 1.51 | 34 | 67 |
| | 10 | - - - - - - - - - - R- L- | 0.297 | 1.06 | | |
| | 20 | - - - R- - - - - - - - L- | 0.292 | 1.06 | | |
| V | Mas19 | - - - A- - - - - - - - L- | 0.196 | 1.51 | 37 | 73 |
| VI | MP-A' | - KW- - I LDAV- - V- | 0.347 | 0.61 | | |
| | T | - - - - - I - - F- - - L- | 0.332 | 1.09 | | |
| | X | - - W- GI - - M- - - L- | 0.322 | 0.53 | | |
| VII | Mas14 | - - - - - - - K- - - - L- | 0.462 | 0.70 | 16 | 64 |
| | 15 | - - - - - - K- - - - - L- | 0.372 | 0.70 | | |
| | 18 | - - - - K- - - - - - - L- | 0.376 | 0.70 | | |
| VIII | Mas11 | - - - - - - - - - K- - L- | 0.223 | 0.70 | 20 | 34 |
| | 13 | - - - - - - - - K- - - L- | 0.278 | 0.56 | | |
| IX | Mas6 | - - - - - - - - - - - - K- | 0.175 | 0.56 | | |
| | 17 | - - - - - K- - - - - - L- | 0.154 | 0.56 | 15 | 31 |

Their abilities to promote GDP exchange by G$_i$ are shown in FIG. 1. This assay, which is completed in about 2 min, was used to avoid the need to determine the effect of each peptide on stability. However, each peptide was also evaluated in a 10-min GTPase assay with similar results.

Regulatory activity was markedly enhanced by eliminating the positive charge at position 12 (Mas7, Lys→Ala) or by delocalization of the charge by replacing lysine with arginine (Mas8). Maximal stimulation by Mas7 was twice as great as stimulation by MP, which typically stimulates G$_i$ about 15-fold in both GTPase and GDP exchange assays. The EC$_{50}$ of Mas7 was also 5-fold lower than that of MP. Removal or delocalization of the positive charges at positions 4 and 11 had similar but smaller effects (groups IV and V). In general, the similarity of the effects of the Lys→Arg and Lys→Ala substitutions were surprising and need to be explored further.

The active MP analogs assumed largely helical conformations in the presence of phospholipid (FIG. 2 and Table I), as does MP. Those structural changes that would be predicted to interfere with formation of the amphipathic α helix or with its binding to the vesicles decreased regulatory activity. Thus, the peptides in groups VIII and IX, which have lysine residues on what should have been the hydrophobic face of the helix, did not form helices in the presence of lipid and were only slightly active. The group VII peptides, with extra lysine residues on the hydrophilic face, and the other natural analogs were only slightly less active than MP.

Figure 2:
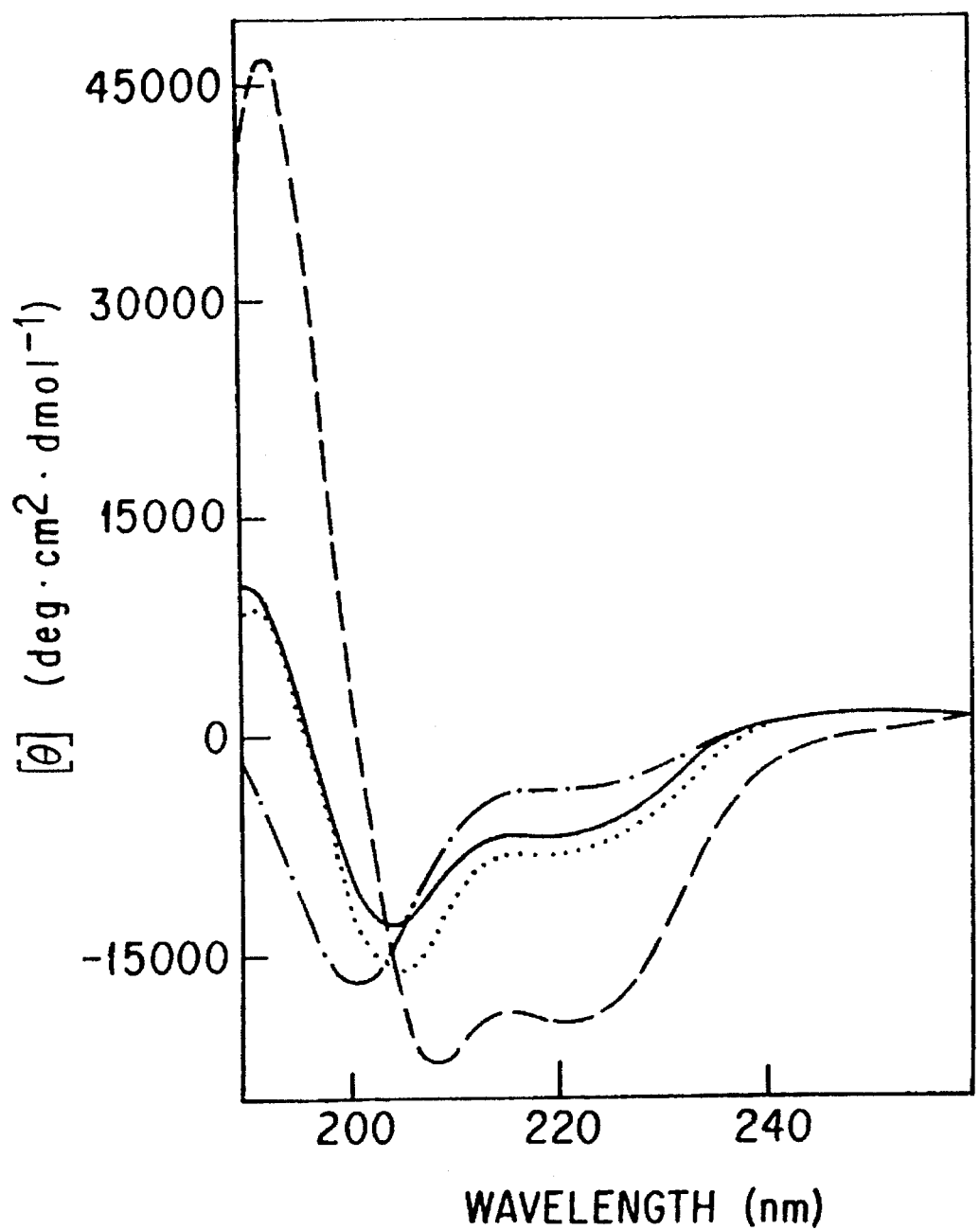
FIG. 2. Circular dichroism spectra of active and inactive MP analogs. Spectra were determined as described under "Experimental Procedures" in the presence or absence of PC. Molar ellipticities are calculated per mol of amino acid residue. Mas7 alone, —; Mas7 plus PC, - - - ; Mas 17 alone, . - . -; Mas17 plus PC, ----.

The pattern of potencies and efficacies shown for G$_i$ in FIG. 2 was similar to that observed for G$_o$ both in GTPase and GDP exchange assays. Preliminary experiments suggest that alterations in the hydrophobic face of the MP structure can alter selectivity between G$_i$ and G$_o$, although no obvious structure-function relationship has emerged from these data.

Structure-Activity Relationships for G Protein Regulation: Biological Peptides Not Related to MP Amphiphilic and cationic peptides are abundant in nature and have diverse biological functions. When an assortment of peptides was tested for their ability to activate G$_i$ and G$_o$, several were found to be quite effective (Table II).

TABLE II

Effects of biological peptides on the GTPase activity of $G_o$ and $G_i$
The GTPase activity of $G_i$ or $G_o$ in PE/PC/PS vesicles was assayed in the presence of each peptide for 30 min at 30° C. ($G_i$) or 15 min at 20° C. ($G_o$). Hydrophobic moments (μ) for some peptides and hydrophobicities, HΦ, are calculated as in Table I. — indicates that 10 μM peptide stimulated exchange by less than 60%. H, histidine, not counted toward net charge, Abbreviations used are DALE, [D-Ala²]Leu-enkephalin; FMPF-amide, Phe-Met-Arg-Phe-NH₂; LHRH, luteinizing hormone releasing hormone; signal-1, signal peptide of the β subunit of F₁ ATPase (MVLPRLYTATSRAAFRAAKIQ); signal-2, LamB signal peptide (MMITLRKLPLAVAVAAGVMSAQAMA); TRH, thyrotropin releasing hormone; CBP6, Ac-WKKLLKLLKKLLKL-NH₂; TRP3, LKWKKLLKLLKKLL-KLG.

| | GTPase | | | | | | |
|---|---|---|---|---|---|---|---|
| | $G_o$ | | $G_i$ | | | | |
| Peptide | 10 μM | 100 μM | 10 μM | 100 μM | μ | Net charge | HΦ |
| | min⁻¹ | | | | | | |
| None | 0.66 | | 0.03 | | | | |
| Mastoparan | 0.59 | 0.95 | 0.19 | 0.47 | 0.331 | +4 | 1.1 |
| CBP6 | 0.76 | 0.38 | 0.51 | 0.06 | 0.712 | +6 | 0.1 |
| TRP3 | 0.63 | 0.54 | 0.44 | 0.09 | 0.523 | +7 | 0.1 |
| Melittin | 0.63 | 0.56 | 0.37 | 0.40 | 0.239 | +6 | 0.4 |
| Gramicidin S | 0.17 | 0.47 | 0.13 | 0.31 | Cyclic | +2 | 1.0* |
| Dynorphin | 0.13 | 0.33 | — | 0.10 | 0.202 | +4 | −1.2 |
| Signal-2 | — | 0.36 | — | 0.06 | 0.065 | +2 | 1.3 |
| Angiotensin II | — | 0.31 | — | 0.23 | 0.0% | 0,H | −4.3 |
| Substance P | — | 0.25 | — | 0.09 | 0.093 | +3 | −0.7 |
| Signal-1 | — | 0.22 | — | 0.08 | 0.245 | +4 | 0.1 |
| α-Mating factor | — | 0.19 | — | 0.05 | 0.138 | +2,H | −0.8 |
| Calcitonin | — | 0.09 | — | 0.01 | 0.139 | +1,H | 0.0 |
| Glucagon | — | 0.08 | — | 0.06 | 0.102 | 0,H | −0.9 |
| FMRF-amide | — | 0.07 | — | 0.04 | 0.511 | +2 | 0.7 |
| TRH | — | 0.06 | — | 0.03 | 0.134 | 0,H | −2.7 |
| DALE | — | 0.06 | — | 0.02 | 0.026 | 0 | 1.3 |
| Melanostatin | — | 0.05 | — | 0.03 | 0.258 | +1 | 0.6 |
| Bradykinin | — | 0.05 | — | 0.03 | 0.165 | +2 | −1.0 |
| LHRH | — | 0.04 | — | 0.03 | 0.349 | +1,H | −1.2 |

*Orn was assigned the hydrophobicity of Lys.

CBP6 and TRP3, two synthetic peptides that were designed to form cationic, amphiphilic α helices were quite active. Melittin, an amphiphilic peptide composed of a hydrophobic region and a cationic hydrophilic region, activated both G proteins with potency and efficacy roughly equivalent to that of mastoparan. Gramicidin S and dynorphin were also somewhat stimulatory at 10 μM. AT higher concentrations, peptides such as angiotensin II, yeast α mating factor, and two signal peptides all stimulated GTPase activity more than 3-fold. Substance P was able to stimulate $G_i$ and $G_o$ more than 4-fold, which is consistent with the proposal that the "non-receptor-mediated" effects of substance P on mast cell secretion may reflect its MP-like stimulation of a G protein.

As a cautionary note, it should be pointed out that almost all of the peptides that were tested caused at least minor stimulation at high concentrations. Activities of the weaker peptides did not correlate closely with either net charge, charge per length or hydrophobic moment. Because even hydrophobic amines (see below) and ammonium sulfate can promote nucleotide exchange on G proteins, arguments for specific structure-function relationships and analogies to the structures of specific receptors must be based on careful studies of concentration dependence and on correlation between regulation of cell function and in vitro stimulation of G proteins.

Inhibition of MP Effects of $G_i$ by BAC

Figure 3:
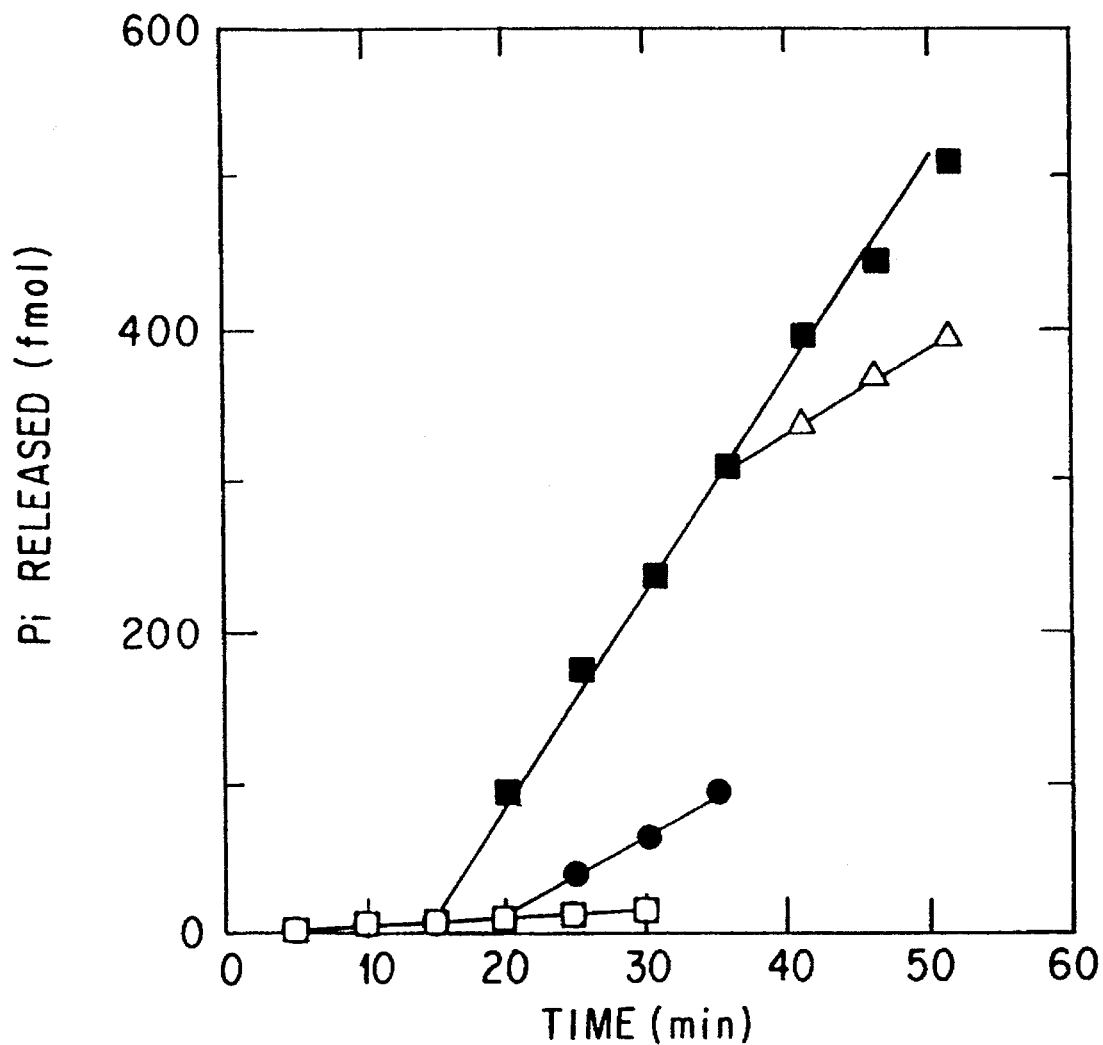
FIG. 3. Inhibition by BAC of the MP-stimulated GTPase activity of $G_i$. The GTPase activity of reconstituted $G_i$ (19.6 fmol/assay) was measured at 30° C. with 200 nM GTP in the presence of 0.1 mM free $Mg^{2+}$ (□). AT 15 min, Mas7 (10 μM final) was added to one of the assay mixtures (■) and, at 35 min, BAC (3 μg/ml) was also added to a portion of this assay mixture ($\Delta$). Another assay was initiated in the presence of 3 μg/ml BAC (○, and 10 μM Mas7 was added to a portion of this assay mixture at 20 min (●).
Figure 4A:
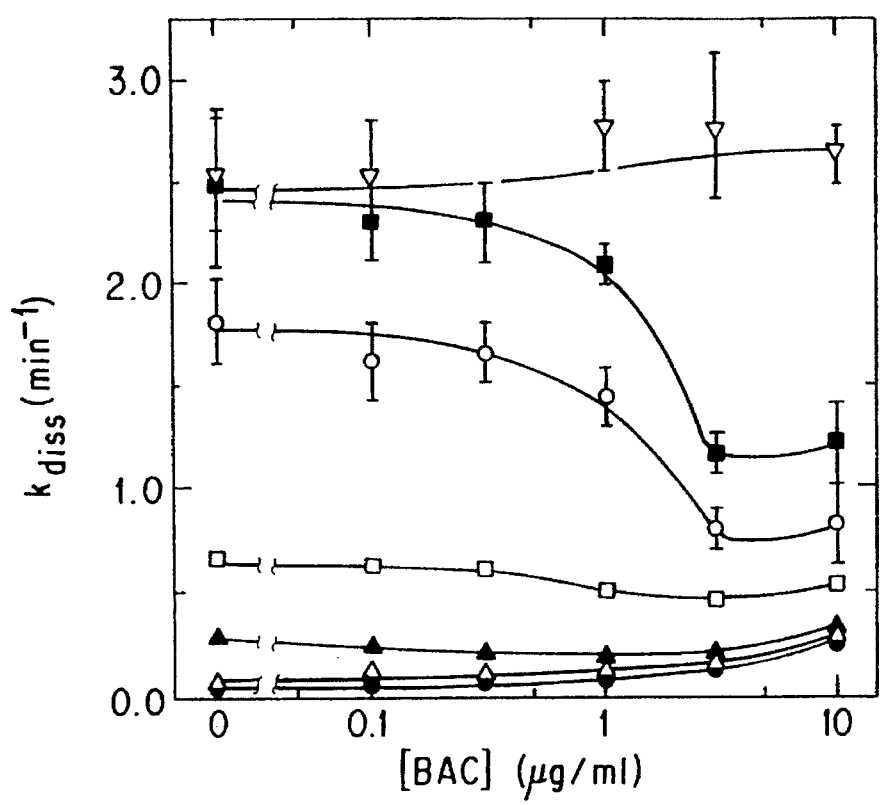
FIG. 4. Inhibition by BAC of MP-stimulated GDP exchange by $G_i$. A, the dissociation of [$\alpha$-$^{32}$P]GDP from 4 nM $G_i$ was measured at 30° C. as described In Example 1 in medium that contained 0.1 mM free $Mg^{2+}$, the concentration of BAC shown on the abscissa, and the following concentrations of Mas7: ●, O; $\Delta$, 1 μM; ▲, 3 μM; □, 10 μM; 0, 20 μM; ■, 30 μM; , 100 μM. Samples were taken between 5 and 120 s, as appropriate, and first order exchange rate constants, $k_{obs}$ were obtained by fitting four pairs of duplicate data points. B, the data from panel A were replotted to show the response to increasing concentrations of Mas7 at the increasing concentrations of BAC. Hill coefficients for stimulation were 2.9±0.8, 3.1±0.7, 3.3±0.7, 2.6±0.9, 2.1±0.4, and 2.2±0.4 at 0 (O), 0.1 (●) 0.3 ($\Delta$), 1 (▲), 3 (□), and 10 (■) μg/ml BAC. The inset shows the change in the concentration of MP7 that produced half-maximal stimulation of GDP exchange ($EC_{50}$) at each concentration of BAC.

The existence of competitive antagonists has traditionally been used to support the existence of specific binding sites for regulatory ligands. BAC is a hydrophobic quaternary amine and antibacterial agent that is known to block histamine secretion from mast cells stimulated by compound 48/80 BAC also antagonized the stimulatory effect of Mas7 and MP on the GTPase activity of $G_i$ (FIGS. 3 and 4). Inhibition was reversible and appeared to be at least partly competitive. However, BAC destablizes G proteins, and the effect of high concentrations of BAC on steady state GTPase activity could not be conveniently studied because the assays became nonlinear.

The concentration-dependent antagonist activity of BAC was analysed using the rapid equilibrium GDP/GDP exchange assay (FIG. 4). At intermediate concentrations of Mas7, BAC inhibited GDP exchange on $G_i$ by as much as 60%, to a final rate that was still about 5-fold greater than the rate measured in the absence of regulator or in the presence of BAC alone. Inhibition was overcome at higher concentrations of Mas7. There was no detectable inhibition of the basal exchange rate, and high concentrations of BAC alone stimulated basal GDP exchange slightly (FIG. 4).

Stimulation of Nucleotide Exchange on $G_o$ by Hydrophobic Amines

Figure 5:
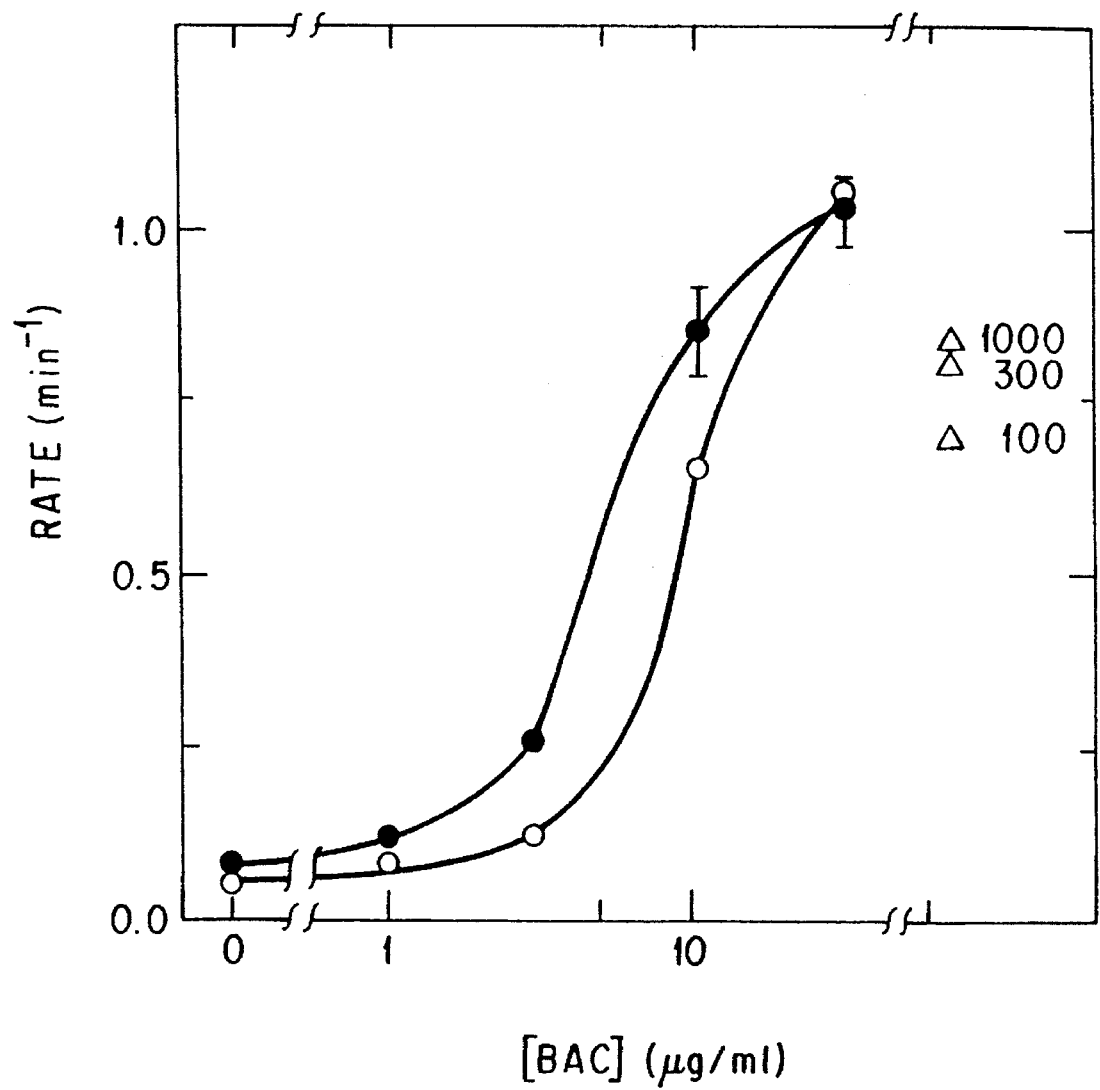
FIG. 5. Stimulation of the steady state GTPase and GDP exchange activity of $G_o$ by BAC. The GTPase activity of 0.93 nM $G_o$ in PE/PC/PS vesicles (3:4:3) was assayed at 100 mM [$\gamma$-$^{32}$P]GTP in the presence of 0, 1, 3, 10 and 30 μg/ml BAC. Activities are shown as molar turnover numbers (O). Rates were taken from linear portions of the time course ranging from 1 to 20 min. For 100, 300, and 1000 μg/ml BAC ($\Delta$; shown at the right), activities were not linear at 1 min. The release of [$\alpha$-$^{32}$P]GDP was also measured under similar conditions. These data are expressed as first order rate constants (●).
Figure 6A:
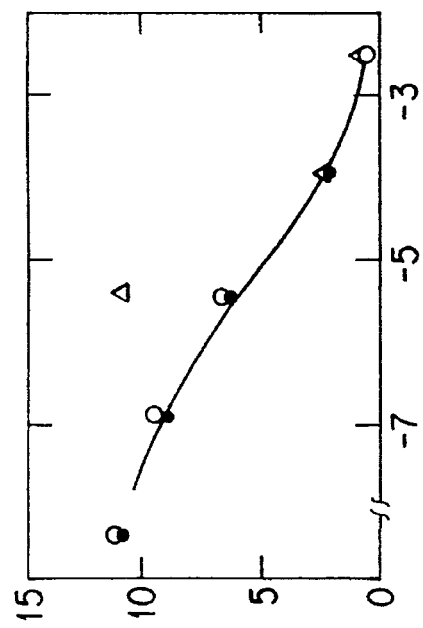
FIG. 6. Effect of MP on the binding of acetylcholine to reconstituted muscarinic receptor. Purified muscarinic cholinergic receptor and $G_o$ were co-reconstituted into phospholipid vesicles, and the binding of acetylcholine (Ach) was measured by competition with the antagonist [$^3$H]QNB as described in Example 1. Assays contained 3.8 nM [$^3$H] QNB. Assays contained, in panel A: 30 μM MP (●) or no addition (O); in panel B: 30 μM Mas 17 (●), 10 μM GTPγS ($\Delta$), or no addition (O); and in panel C: 30 μM Mas7 (●), 10 μM GTPγS($\Delta$), or no addition (O). Panel D shows the binding of acetylcholine to receptors reconstituted into vesicles without G protein ●, 30 μM MP; $\Delta$, 10 μM GTPγS; O, no addition. The data represent the means of duplicate determinations of specific binding.
Figure 6B:
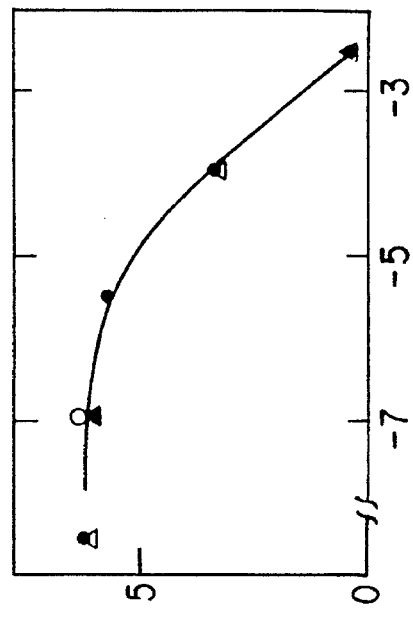
Figure 6C:
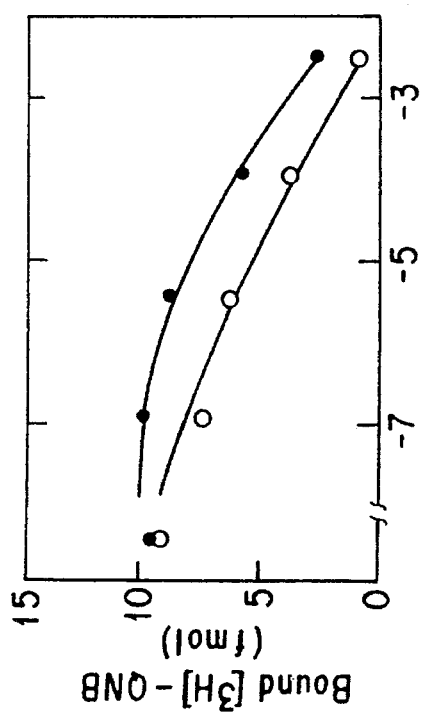
Figure 6D:
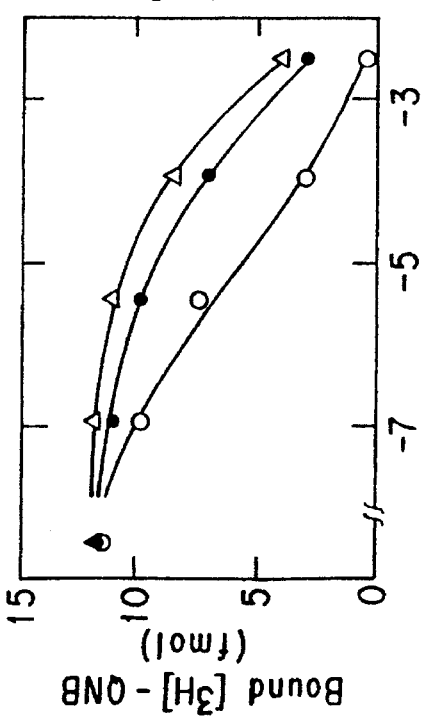

In contrast to its MP-antagonist activity on $G_i$, BAC and several other quaternary amines actually stimulated the nucleotide exchange and GTPase activities of $G_o$ (FIG. 5 and Table III).

TABLE III

Effects of BAC and other alkylamines on $G_o$ and $G_i$
The GTPase activity of $G_i$ or $G_o$ PE/PC/PS vesicles was assayed in the presence of each amine under the conditions described in the legend to Table II. No effect of amines was observed at 1 μg/ml. BAC (benzalkonium chloride), benzyldimethylalkylammonium chloride with alkyl chain length shown. The $C_{12}$ BAC (Sigms) is heterogeneous. Me, methyl; Bz, benzyl; Bu, butyl.

| | Turnover number | | | |
|---|---|---|---|---|
| | $G_o$ | | $G_i$ | |
| Amine | 10 μg/ml | 100 μg/ml | 10 μg/ml | 100 μg/ml |
| | $min^{-1}$ | | | |
| None | 0.07 | | 0.04 | |
| BAC ($C_{-12}$) | 0.33 | 0.8 | 0.08 | 0.04 |
| BAC ($C_{14}$) | 0.9 | 0.2 | 0.04 | <0.01 |
| BAC ($C_{16}$) | 1.4 | 0.08 | 0.04 | <0.01 |
| BAC ($C_{18}$) | 1.1 | 0.3 | 0.03 | <0.01 |
| BzBu$_3$NCl | 0.07 | 0.07 | 0.04 | 0.04 |
| $C_{12}Me_3$NCl | 0.1 | 0.5 | 0.04 | 0.04 |
| $C_{18}Me_3$NCl | 0.61 | <0.01 | 0.04 | <0.01 |
| $C_{12}NH_3$Cl | 0.18 | 0.61 | 0.06 | 0.31 |

Stimulation was dependent on the concentration of phospholipid, as was true for MP. In the experiment shown in FIG. 5, 20-fold maximal stimulation was observed at about 30 μg/ml (~0.1 mM) BAC. Hydrophobic amines markedly destablized G proteins, however, and regulation was difficult to quantitate at high concentrations. Above 30 μg/m BAC, the apparent rate of [α-$^{32}$P]GDP release increased sharply because of denaturation, and the GTPase rate declined, even when measured over only 1 min. Stimulation by BAC was also slight and not well reproducible unless the G protein was reconstituted into phospholipid vesicles.

The requirement for reconstitution may reflect both actual stabilization of $G_o$ by the lipid and the ability of the bilayer to buffer the local concentration of detergent.

Several amines stimulated the GTPase activity of $G_o$ (Table III). Among the BACs, increasing alkyl chain length increased potency but did not have an obvious effect on maximal stimulation. Potency may reflect the tendency of the BAC to partition into the bilayer at low concentrations. The concentration-dependent stimulation of the GDP exchange rate by different BACs, which would provide more informative data on maximum effects, has not yet been elucidated. Other long chain alkylamines, primary through quaternary, stimulated $G_o$, but short chain amines were ineffective. Of the compounds tested, only dodecylamine stimulated $G_i$ significantly.

Figure 4B:
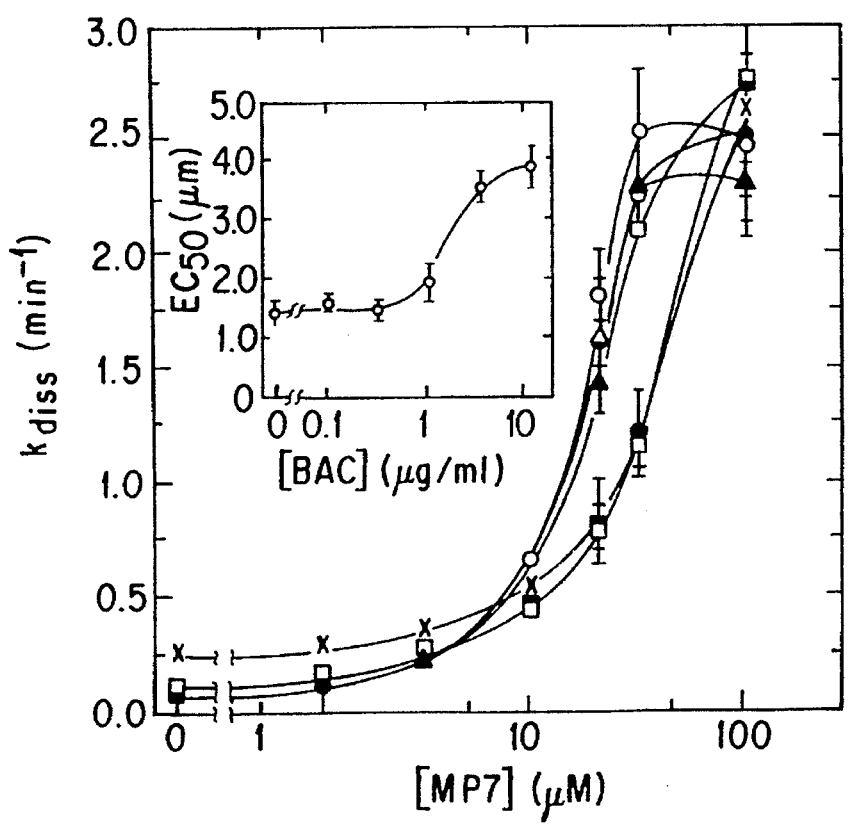

Apparent Positive Cooperativity of G Protein Regulation by Cationic Amphiphiles Under most experimental conditions, MP and other amphiphilic G protein regulators exerted their effects over a narrow range of concentrations (FIGS. 1 and 4B). The concentration dependence on BACs for the stimulation of $G_o$ was also sharp (Table III and FIG. 5). These steep responses are described by Hill coefficient of 2–4 for MP and its analogs. Examples for Mas7 are shown in FIG. 4B. Such responses suggest that 2–4 molecules of amphiphilic peptide may be required for the productive regulation of G protein. These apparently cooperative effects of stimulatory and inhibitory amphiphiles may indicate either that multiple molecules must bind to distinct sites on a G protein or that the formation of a dimer, trimer, or tetramer is required for activity, whether stimulatory or inhibitory. Spontaneous formation of an oligomer of strongly cationic species seems unlikely because the concentrations of MP used here are well below that at which aggregates form. Practically, changes in nucleotide exchange rates over narrow ranges of concentration have made detailed kinetic analyses difficult. It is likely that the mechanism that underlies the high Hill coefficient will have to be determined by independent physical probes.

The inhibitory effect of BAC on G, also yielded a steep concentration curve, as determined by monitoring the concentration of BAC needed to decrease the potency with which Mas7 stimulated nucleotide exchange (FIG. 4B). The $EC_{50}$ for Mas7 increased sharply in the range of 1–3 μg/ml BAC. However, both inhibition by BAC of the stimulation of $G_i$ by MP (FIG. 4) and maximal stimulation of $G_o$ by BAC (FIG. 5) occurred near the critical micelle concentration of 20 μg/ml, and their interpretation is therefore unclear.

Effect of MP on the G Protein-induced Increase in the Affinity of Muscarinic Receptors for Agonists G proteins increase the affinity of receptors for agonist, but not antagonist, ligands. This increase reflects the formation of a G protein-receptor-agonist complex. It is reversed by addition of excess guanine nucleotide or, frequently, by solubilization of the membrane in which the receptor and G protein reside. If MP binds to G proteins at or near the receptor binding site, it might be expected to interfere with the formation of the complex. FIG. 6 shows the effect of MP on the binding of acetylcholine to purified muscarinic cholinergic receptor that was co-reconstituted into phospholipid vesicles with $G_o$. Binding was measured by competition with the antagonist [$^3$H]QNB. Both MP and a highly active MP analog, Mas7, decreased the receptor's affinity for acetylcholine to nearly the same extent as did 10 μm GTPγS. An inactive analog of MP, Mas17, had no effect on acetylcholine binding. If receptor was reconstituted into vesicles without G protein, only low affinity binding of acetylcholine was observed, and neither MP nor guanine nucleotides had any effect on acetylcholine binding. MP did not alter the affinity of the receptor for the antagonist [$^3$H]QNB or the shape of the [$^3$H]QNB binding isotherm when assayed using receptor-$G_o$ vesicles.

DISCUSSION

MP and related G protein regulators are potentially useful as cellular probes of G protein function and as structural models of the G protein-activating domains of the much larger receptors. To fulfill this promise, however, the mechanism of their action must be understood and the structural determinants of their potency and selectively among G proteins must be identified.

Mechanism—By enzymological criteria, MP facilitates nucleotide exchange by a mechanism similar to that utilized by G protein-coupled receptors. MP promoted the dissociation of either GDP or GTPγ from either $G_i$ or $G_o$ in the virtual absence of $Mg^{2+}$ and did not alter the rate of hydrolysis of bound GTP. The effect of MP on the dissociation of GTPγ was much smaller than its effect on the dissociation GTP. This phenomenon is consistent with the knowledge that GDP competes poorly with GTPγS for mascarinic receptor-stimulated binding to $G_o$.

The $Mg^{2+}$-independent effects of MP on GDP release are adequate to account for the stimulation by MP of steady state GTPase activity at submicromolar $Mg^{2+}$. Similar dependencies of GTPase activity on low concentrations of $Mg^{2+}$ have been observed for the stimulation of $G_s$ by the β-adrenergic receptor, of $G_{i,2}$ by the $D_2$ dopamine receptor, and of $G_i$ by the muscarinic cholinergic receptor.

The $Mg^{2+}$ independence of MP-stimulated nucleotide exchange suggests that the only requirement for $Mg^{2+}$ in the overall GTPase cycle is in the conversion of the G protein-GTP complex to the activated form. This step immediately precedes hydrolysis of the bound GTP, and it is assumed that hydrolysis also requires bound $Mg^{2+}$. The interacting effects of $Mg^{2+}$ and MP on GTPase activity suggest that there are two sites at which $Mg^{2+}$ binds G proteins. Binding at the high affinity site allows activation and hydrolysis, and binding at the low affinity site promotes nucleotide exchange in the absence of MP (or receptor).

The inhibitory effect of high concentrations of $Mg^{2+}$ on MP-stimulated steady state GTPase activity and MP-stimulated dissociated of GDP from free α subunit remains unexplained.

Structures of Regulatory Compounds—The data of FIG. 1 and Tables I and II delineate structural features that are required for catalysis of nucleotide exchange on G proteins. Regulatory activity appears to require a minimum length, positive charge, and a combination of net hydrophobicity and hydrophobic moment that is sufficient to allow binding to the bilayer in a way that orients the charge toward the G protein. In the case of Mp and its analogs, this cluster of charge is apparently formed from one face of an amphiphilic helix whose folding is induced when MP binds to a micelle or vesicle (FIG. 2). Other secondary structures can also form such cationic clusters at the surface of bilayers, however.

Within the MP analogs, increasing either hydrophobicity or hydrophobic moment enhanced potency and maximal regulatory activity, although the dominance of one parameter over the ocher was not clear. The most active analogs were those in which Lys was replaced by either Arg or Ala, with substitution at position 12 being most effective. It was surprising that these two replacements for lysine were approximately equal in activity. the increased activity of the Arg-containing analogs may reflect the greater delocalization of charge in the guanidino group of arginine relative to the primary amino group of lysine. Delocalization of charge increases functional hydrophobicity. Thus, while the Lys→Ala substitutions increased hydrophobicity more than Lys→Arg, the Lys→Arg substitutions would delocalize one of the positive charges and also maintain a high hydrophobic moment. Similarly, CBP6, TRP3, and melittin are far less hydrophobic than the MP analogs according to amino acid composition, but their strong amphiphilicity causes them to be membrane-bound and to present a high cationic charge density at the bilayer surface.

It is likely that G proteins are stimulated specifically by the α-helical conformation of MP which forms readily at the surface of micelles or bilayers but not in aqueous solution. Thus, the group VIII and IX analogs, with charge oriented toward what would be the wrong side of the helix, were far less active than MP. They did not form α helices in the presence of phospholipids (FIG. 2, Table I). The group VII analogs, with one extra charge oriented toward the putative hydrophilic face, did form α helices and were similar to MP in regulatory activity. The dependence of P potency on the concentration of phospholipid also implies that the surface of the bilayer is actually the relevant solvent for these peptides.

Mp and other amphiphilic G protein regulators are attractive as cellular probes for the signaling activities of individual G proteins. Although a concentration of positive charge at the surface of the bilayer is apparently necessary for the catalysis of nucleotide exchange by G proteins, the different responses of $G_i$ and $G_o$ to the compounds tested here argue for structural specificity and the possibility of designing compounds that will be highly selective among the homologous G proteins. The observation that BAC stimulates $G_o$ but antagonizes the effect of MP on $G_i$ is a strong argument for specific and selective binding of cationic regulators to G proteins. Because BAC inhibits the stimulation of histamine secretion from mast cells, this finding also suggests that $G_i$ is the most plausible target of MP in these cells. Another example of selectivity is that $G_s$ and transducin are far less sensitive to MP than are $G_o$ and $G_i$, while a Trp,Arg copolymer strongly stimulates $G_s$ but stimulates $G_i$ and $G_o$ only slightly. These data all suggest that amphiphilic, cationic peptides bind to a negatively charged site (or sites) on G proteins, but that the detailed structure of the site is selective among cationic ligands.

The regulation of G proteins by MP and by receptors appear to be similar in many ways. If MP actually is a structural analog of the regulatory domain of G protein-coupled receptors, then MP should compete with receptors for binding to a common site on G proteins. Such a model predicts data of the sort shown in FIG. 6 because MP should compete for $G_o$ with the receptor, a known regulator of $G_o$ and thus block the ability of $G_o$ to enhance the affinity with which the receptor binds agonists. The data of FIG. 6, while provocative, do not prove that MP and the receptor are actually competing for $G_o$. Minimal proof would require demonstrating that increasing concentrations of $G_o$ can appropriately overcome the effects of increasing concentrations of MP. These experiments are limited by the need for high concentrations of G protein to regulate the binding of the mascarinic receptor and by the relatively low potency of the currently available MP analogs. Competition between receptors and MP for binding to G protein will more likely be demonstrated through direct binding assays or the use of MP-based antagonists.

The analogy between the MPs and the intracellular loops of the G protein-coupled receptors suggests that a cationic, amphipathic structure formed from one or more of these loops comprises the activating site on a receptor's cytoplasmic surface. This idea is consistent with the results of genetic and chemical manipulations of these domains in the receptors. We do not know whether this functionally defined "site" corresponds to a single structural region on a receptor or whether several cationic regions must be appropriately presented for G protein regulation to occur. The latter idea would account for the high ill coefficients that we observed for the MPs and is consistent with the ability of independent mutations into short regions of the M1-muscarnic cholinergic receptor to alter selectivity between G proteins. Regardless, the ability to design MP analogs with varying activities and selectivities and the relative ease with which their three-dimensional structure can be determined argue for their continued application to the question.

EXAMPLE 2

This example relates to the regulation of $G_o$, $G_i$ and $G_s$ by modified mastoparan-based peptides and synthetic peptides corresponding to intracellular loops of G protein-receptors. In particular, the present example provides an investigation and analysis of various peptides of the invention, along with their apparent affinity and efficacy.

G-protein-coupled receptors share a structural motif which is characterized by 7 hydrophobic domains, thought to represent membrane-spanning helices, connected by more hydrophilic extracellular and intracellular loops. Genetic and biochemical analyses of several of these receptors suggests that the intracellular loop domains mediate the coupling of the receptors with G proteins. Deletion mutagenesis and hybrid receptor analysis have implicated regions at the N- and C-terminal ends of the third intracellular loop as the major, but not the sole, determinants of G protein coupling.

Secondary structure predictions suggested to the inventors that the regions at the N- and C-terminal ends of this loop may be α-helical in nature, forming amphipathic cytoplasmic extensions of transmembrane helices 5 and 6. However, there is no consensus amino acid sequence in this region from which coupling to a specific G protein can be predicted. The lack of primary sequence homology in this region among receptors which couple to the same G protein has led to the hypothesis that it is the amphiphilic and cationic nature of these α-helical regions that is the main determinant in the interaction of receptors with G proteins. This is in keeping with the structure and activity of the mastoparans, which form amphiphilic helices, parallel to the plane of the membrane, when binding to a phospholipid bilayer.

The following studies were designed to demonstrate and further delineate the structure-activity relationships for the regulation of G proteins by mastoparans, and to compare their activity with synthetic peptides corresponding to intracellular loops of various receptors. Furthermore, the effect of specific modifications on the activity of the receptor-based peptides was investigated.

The data set forth in the following tables represent data generated by the inventors employing the steady state GTP hydrolysis, expressed as molar turnover numbers, are described herein under the "Assay" section of the Experimental Procedures in Example 1. The data has been classified according to the criteria outlined below and the effects of each peptide and modified variant on $G_o$, $G_i$, and $G_s$ have been tabulated. Table III below sets forth data generated for various mastoparan analogues designed by the inventors, in comparison with the various naturally-occurring mastoparans (e.g., MP, MP-A and MP-T). Table IV sets forth similar data generated for various receptor-based peptides designed by the inventors based on a consideration of various G-protein linked receptors.

Apparent affinity (af.) and apparent efficacy (ef.) were estimated by $EC_{50}$ and maximum turnover number of GTPase activity.

For affinity:
  Super (S): less than 3 μM
  Excellent (E): 3–10 μM
  Good (G): 10–30 μM
  Fair (F): 30–100 μM
  Poor (P): more than 100 μM For efficacy:
  Super (S): more than 30-fold
  Excellent (E): 30–10 fold
  Good (G): 5–10 fold
  Fair (F): 2–5 fold
  Poor (P): less than 2 fold For MAS peptides, GDP-dissociation as well as GTP-hydrolysis were observed, and basically similar results were obtained.

TABLE IV

| | | $Go_o$ | | $G_i$ | | $G_s$ | |
|---|---|---|---|---|---|---|---|
| | | af. | ef. | af. | ef. | af. | ef. |
| MP | INLKALAALAKKIL-NH$_2$ | E | E | G | E | E | F |
| MP-A | -KW- - I LDAV- - V- | E | E | E | G | E | F |
| MP-T | - - - - - I - - F - - - L- | E | E | E | E | G | F |
| MAS03 | - - - - - - - - - - - L- | E | E | G | E | G | F |
| MAS04 | - - - - - - - - - - - LA | E | E | G | G | E | F |
| MAS05 | - - - - - - - - - - - A- | G | G | G | F | G | F |
| MAS06 | - - - - - - - - - - - K- | F | F | F | F | F | F |
| MAS07 | - - - - - - - - - - AL- | E | S | E | S | E | F |
| MAS08 | - - - - - - - - - - RL- | E | E | E | E | E | F |
| MAS0E | - - - - - - - - - A- L- | E | E | E | E | F | F |
| MAS10 | - - - - - - - - - R- L- | E | E | G | E | E | F |
| MAS11 | - - - - - - - - - K- - L- | G | G | E | F | E | F |
| MAS12 | - - - - - - - - A- - - L- | G | E | F | G | E | F |
| MAS13 | - - - - - - - - K- - - L- | F | G | F | G | E | F |
| MAS14 | - - - - - - - K- - - - L- | G | E | E | G | E | F |
| MAS15 | - - - - - - K- - - - - L- | G | E | G | G | E | F |
| MAS16 | - - - - - A- - - - - - L- | G | E | F | G | E | F |
| HAS17 | - - - - - K- - - - - - L- | F | F | P | P | E | F |
| MAS18 | - - - - K- - - - - - - L- | G | E | G | G | E | F |
| HAS19 | - - - A- - - - - - - - L- | E | E | E | E | E | F |
| MAS20 | - - - R- - - - - - - - L- | E | E | E | E | E | F |
| MAS21 | - - A- - - - - - - - - L- | G | E | F | E | G | F |
| MAS22 | - - F- - - - - - - - - L- | G | E | G | E | E | F |
| MAS23 | - - - - - F- - - - - - L- | G | E | G | E | E | F |
| MAS24 | - - - - - - - - - - - L- | E | E | G | E | G | F |
| ER1 | INLKALAALAKALL-NH$_2$ | E | S | E | S | E | F |
| ER2 | - - - - - - - - - - R- - - | S | E | E | S | E | F |
| ER3 | - - - - - - - - - - Q- - - | G | E | G | S | E | F |
| ER4 | - - - A- - - - - - - - - | E | E | G | S | E | F |
| ER5 | - - - - - - - - - - A- - - | E | E | G | S | E | F |
| ER6 | - - - R- - - - - - - - - | S | E | E | S | E | F |
| ER7 | - - - R- - - - - - R- - - | S | S | E | S | E | F |
| ER8 | - - - Q- - - - - - - - - | E | S | E | S | E | F |
| ER9 | - - - Q- - - - - Q- - - | F | G | P | F | G | F |
| ER10 | - - - - - - K- - - - - - - | S | S | E | S | E | F |
| ER11 | - - - Q- - K- - - - - - - | E | E | E | S | E | F |
| ER12 | - Q- - - - - - - - - - - | E | E | E | S | E | F |
| ER13 | - - Y- - - - - - - - KI- | E | E | G | E | E | F |

TABLE IV-continued

|  |  | G$_o$ | | G$_i$ | | G$_s$ | |
|---|---|---|---|---|---|---|---|
|  |  | af. | ef. | af. | ef. | af. | ef. |
| ER14 | - - Y- - - - - C- - KI - | E | E | G | E | E | F |
| ER15 | - - Y- - - C- - - - KI - | F | G | G | G | G | F |
| ER16 | C- Y- - - - - - - - - - - | E | E | E | S | G | F |
| C12-ER16 |  | S | E | S | S | E | F |
| C16-ER16 |  | S | E | S | S | E | F |
| ER17 | - - Y- - - - - - - - - - C | E | E | E | E | G | F |
| C12-ER17 |  | S | E | S | S | E | F |
| C16-ER17 |  | S | E | S | E | E | F |
| ER20 | - - - - - - - - - - - - N- - | E | E | G | E | G | F |
| ER21 | - L- - - - - - - - - - - - | E | E | E | S | E | E |
| ER24 | - - - R- - R- - - R- - - | S | E | E | S | E | F |
| ER25 | - - - - - - - - - - K- - - - | G | E | G | E | G | F |
| ER27 | - -WR- WR- W- R- W- | S | P | E | G | E | P |
| ER28 | - - - R- - - - - RRR- - | S | G | G | F | E | P |
| ER29 | - - - - - - - - - K- K- - (=MAS 11) | G | G | G | G | E | F |
| ER30 | CL- - - - - - - - - - - - | E | G | E | E | E | E |
| C12-ER30 |  | S | G | S | E | E | F |
| ER26 | AcLTAVLLTLTLLLYR<u>INLKALAALAKA</u><u>LL</u>-NH$_2$ | E | F | E | G | E | F |

The peptides of this table are represented by seq id nos: 66–68, 1–21, 1, and 22–47, respectively.

TABLE V

| | Sequencee and Explanation of Receptor-Based Peptides | |
|---|---|---|
| ER18 | CVYREAKEQIRKIDRVL-NH$_2$ | turkey β-I3N |
| ER19 | CVYREAKEQIRKIL-NH$_2$ | turkey β-I3N |
| ER22 | IVYREAKEQIRKIDRVL-NH$_2$ | turkey β-I3N |
| ER23 | IVYREAKEQIRKIL-NH$_2$ | turkey β-I3N |
| ER32 | CIYRETENRARELAALQGSET-KH2 | M1-I3N |
| ER33 | CIYRETENRARELAALQGSETIL-NH$_2$ | M1-I3N |
| ER34 | CVYIVAKRTTKNLEAGVMKEIL-NH$_2$ | Ha-α1-I3N |
| ER35 | CVYIVAKRTTKNLEIL-NH$_2$ | Ha-α1-I3N |
| ER36 | CVFQVAKRQLQKIDKVL-NH$_2$ | Ha-β2-I3N |
| ER37 | Ac-ER-36 | Ha-β2-I3N |
| ER38 | CPLSYRAKRTPRRAALM-NH$_2$ | M1-I2 |
| ER39 | CPFRYQSLNTRARAKVI-NH$_2$ | turkey β-I2 |
| ER40 | REHKALKTLGIIC-NH$_2$ | turkey β-I3C |
| ER41 | CRSPDFRKAPKRLLC-NH$_2$ | turkey β-I4N |
| ER42 | Ac-ER-41 | turkey β-I4N |
| ER43 | CVYREAKEQIRKIDR-NH$_2$ | turkey β-I3N w/o IL |
| ER44 | CISRASKSRIKKDKKEPVAIL-NH$_2$ | Ms-I3N |
| ER45 | CISRASKSRIKKDKKIL-NH$_2$ | M2-I3N |
| ER46 | CVYVVAKRESRGLKSGLKTDIL-NH | COW A1-I3N |
| ER47 | CVYVVAKRESRGLKIL-NH$_2$ | COW A1-I3N |

The peptide sequences of this table represent seq id nos: 48–65, respectively.

TABLE VI

|  | G$_o$ | | G$_i$ | | G$_s$ | |
|---|---|---|---|---|---|---|
|  | af. | ef. | af. | ef. | af. | ef. |
| ER18 | F | F | G | F | P | F |
| C12-ER18 | G | F | G | G | E | F |
| ER19 | P | F | G | F | P | P |
| C12-ER19 | G | F | G | G | E | E |
| ER22 | F | F | F | F | F | F |
| ER23 | F | F | F | F | F | F |
| ER32 | P | P | P | P | P | P |
| C12-ER32 | P | P | P | P | P | P |
| ER33 | P | P | P | P | P | P |
| C12-ER33 | P | P | P | P | P | P |
| ER34 | F | F | G | F | F | F |
| C12-ER34 | S | G | E | G | F | G |
| ER35 | G | F | F | F | P | P |
| C12-ER35 | G | F | G | F | G | F |
| ER36 | G | F | G | F | F | E |
| C12-ER36 | S | G | S | G | E | G |
| ER38 | E | F | G | F | F | F |
| C12-ER38 | G | F | E | G | F | P |
| ER39 | F | F | P | F | F | F |
| C12-ER39 | E | G | E | G | F | F |
| ER40 | P | P | P | P | F | F |
| C12-ER40 | E | F | E | G | E | F |
| ER43 | P | P | P | P | P | P |
| C12-ER43 | G | F | G | F | G | F |

TABLE VI-continued

|         | $G_o$ |     | $G_i$ |     | $G_s$ |     |
|---------|-------|-----|-------|-----|-------|-----|
|         | af.   | ef. | af.   | ef. | af.   | ef. |
| ER44    | S     | F   | P     | P   | F     | F   |
| C12-ER44| S     | F   | E     | F   | F     | F   |
| ER45    | S     | F   | P     | P   | E     | F   |
| C12-ER45| G     | F   | E     | F   | F     | F   |
| ER46    | F     | F   | E     | F   | P     | P   |
| C12-ER46| F     | F   | G     | G   | F     | F   |
| ER47    | F     | F   | P     | F   | P     | P   |
| C12-ER47| P     | P   | G     | P   | F     | F   |

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

REFERENCES

The following references, to the extent that they supplement, explain or provide a basis for, techniques disclosed or referred to herein are hereby incorporated by reference Bokoch, et al. (1984), *J. Biol. Chem.*, 259:3560–3567
Brandt and Ross (1986), *J. Biol Chem.*, 261:1656–1664
Brandt, et al. (1983), *Biochemistry*, 22:4357–4362
Ferguson, et al. (1986), *J. Biol. Chem.*, 261:7393–7399
Fleming & Ross (1980), *J. Cyclic Nucleotide Res.*, 6:407–419
Haga, et al. (1985), *Nature*, 316:731–733
Haga, et al. (1986), *J. Biol. Chem.* 261:10133–10140
Haga and Haga (1985), *J. Biol. Chem.*, 260:7927–7935
Higashijima, et al. (1987), *J. Biol. Chem.*, 262:757–761
Higashijima, et al. (1987), *J. Biol. Chem.*, 262:752–756
Higashijima, et al. (1990), *J. Biol. Chem.*, 265(24):14176–14186
Higashijima et al. (1988), *J. Biol. Chem.*, 263:6491–6494
Linder (1990), *J. Biol. Chem.* 265:8243–8251
Mumby, et al. (1983), *J. Biol. Chem.*, 258:11361–11368
Mumby, et al. (1988), *J. Biol. Chem.*, 263:2020–2026
Northup (1983) *J. Biol. Chem.*, 258:11361–11368
Saito, et al. (1984), *Chem. Pharm. Bull.*, 32:2187–2193
Schrock and Gennis, (1977), *J. Biol. Chem*, 252:5990–5995
Sternweis, et al. (1981), *J. Biol. Chem.*, 256:11517–11526
Sternweis and Robishaw (1984), *J. Biol. Chem.*, 259:13806–13813
Wong, et al. (1990), *J. Biol. Chem.*, 265:6219–6224

What is claimed is:

1. A peptide other than MP, MP-A or MP-T, the peptide being from 12 to 26 amino acids in length and including within its structure a G protein modulator region comprising:

a) a mastoparan analog region including the following formula:

$$AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}\text{-}AA_{12}$$
(Seq id no:70)

wherein:
$AA_1$ = L, W, A, F or Y;
$AA_2$ = K, A, R or Q;
$AA_3$ = A or K;
$AA_4$ = L, W, I, A, K or F;
$AA_5$ = A, L, K, C or R;
$AA_6$ = A, D or K;
$AA_7$ = L, C,, W, A, F or K;
$AA_8$ = A, V, K or R;
$AA_9$ = K, R, Q or A;
$AA_{10}$ = K, A, R or N;
$AA_{11}$ = L, I,, W, V, A or K; and
$AA_{12}$ = L, A or C; or b) a receptor analog region comprising CVYREAKEQIRKIDRVL (Seq id no:48); CVYREAKEQIRKIL (Seq id no:49); IVYREAKEQIRKIDRVL (Seq id no:50); IVYREAKEQIRKIL (Seq id no:51); CIYRETENRARELAALQGSET (Seq id no:52); CIYRETENRARELAALQGSETIL (Seq id no:53); CVYIVAKRTTKNLEAGVMKEIL (Seq id no:54); CVYIVAKRTTKNLEIL (Seq id no:55); CVFQVAKRQLQKIDKVL (Seq id no:56); CPLSYRAKRTPRRAALM (Seq id no:57); CPFRYQSLMTRARAKVI (Seq id no:58); REHKALKTLGIIC (Seq id no:59); CRSPDFRKAFKRLLC (Seq id no:60); CVYREAKEQIRKIDR (Seq id no:61); CISRASKSRIKKDKKEPVAIL (Seq id no:62); CISRASKSRIKKDKKIL (Seq id no:63); CVYVVAKRESRGLKSGLKTDIL (Seq id no:64); or CVYVVAKRESRGLKIL (Seq id no:65).

2. The peptide of claim 1, wherein the peptide comprises a G protein modulator mastoparan analog region including the following structure:

$$AA_A\text{-}AA_B\text{-}AA_1\text{-}AA_2\text{-}AA_3\text{-}AA_4\text{-}AA_5\text{-}AA_6\text{-}AA_7\text{-}AA_8\text{-}AA_9\text{-}AA_{10}\text{-}AA_{11}AA_{12}$$
(seq id no:71)

$AA_A$ = I or C;
$AA_B$ = N, K, Q or L;
$AA_1$ = L, W, A, F or Y;
$AA_2$ = K, A, R or Q;

AA₃=A or K;
AA₄=L, W, I, A, K or F;
AA₅=A, L, K, C or R;
AA₆=A, D, or K;
AA₇=L, C,, W, A, F or K;
AA₈=A, V, K or R;
AA₉=K, R, Q or A;
AA₁₀=K, A, R or N;
AA₁₁=L, I, W, V, A or K; and
AA₁₂=L, A or C.

3. The peptide of claim 1, wherein the analog region comprises LKALAALAKKLL of seq id no:1.
4. The peptide of claim 1, wherein the analog region comprises LKALAALAKKLA of seq id no:2.
5. The peptide of claim 1, wherein the analog region comprises LKALAALAKKAL of seq id no:3.
6. The peptide of claim 1, wherein the analog region comprises LKALAALAKKKL of seq id no:4.
7. The peptide of claim 1, wherein the analog region comprises LKALAALAKALL of seq id no:5.
8. The peptide of claim 1, wherein the analog region comprises LKALAALAKRLL of seq id no:6.
9. The peptide of claim 1, wherein the analog region comprises LKALAALAAKLL of seq id no:7.
10. The peptide of claim 1, wherein the analog region comprises LKALAALARKLL of seq id no:8.
11. The peptide of claim 1, wherein the analog region comprises LKALAALKKKLL of seq id no:9.
12. The peptide of claim 1, wherein the analog region comprises LKALAAAAKKLL of seq id no:10.
13. The peptide of claim 1, wherein the analog region comprises LKALAAKAKKLL of seq id no:11.
14. The peptide of claim 1, wherein the analog region comprises LKALAKLAKKLL of seq id no:12.
15. The peptide of claim 1, wherein the analog region comprises LKALKALAKKLL of seq id no:13.
16. The peptide of claim 1, wherein the analog region comprises LKAAAALAKKLL of seq id no:14.
17. The peptide of claim 1, wherein the analog region comprises LKAKAALAKKLL of seq id no:15.
18. The peptide of claim 1, wherein the analog region comprises LKKLAALAKKLL of seq id no:16.
19. The peptide of claim 1, wherein the analog region comprises LAALAALAKKLL of seq id no:17.
20. The peptide of claim 1, wherein the analog region comprises LRALAALAKKLL of seq id no:18.
21. The peptide of claim 1, wherein the analog region comprises AKALAALAKKLL of seq id no:19.
22. The peptide of claim 1, wherein the analog region comprises FKALAALAKKLL of seq id no:20.
23. The peptide of claim 1, wherein the analog region comprises LKAFAALAKKLL of seq id no:21.
24. The peptide of claim 1, wherein the analog region comprises LKALAALAKALL of seq id no:22.
25. The peptide of claim 1, wherein the analog region comprises LKALAALARALL of seq id no:23.
26. The peptide of claim 1, wherein the analog region comprises LKALAALAQALL of seq id no:24.
27. The peptide of claim 1, wherein the analog region comprises LAALAALAKALL of seq id no:25.
28. The peptide of claim 1, wherein the analog region comprises LKALAALAAALL of seq id no:26.
29. The peptide of claim 1, wherein the analog region comprises LRALAALAKALL of seq id no:27.
30. The peptide of claim 1, wherein the analog region comprises LRALAALARALL of seq id no:28.
31. The peptide of claim 1, wherein the analog region comprises LQALAALAKALL of seq id no:29.
32. The peptide of claim 1, wherein the analog region comprises LQALAALAQALL of seq id no:30.
33. The peptide of claim 1, wherein the analog region comprises LKALKALAKALL of seq id no:31.
34. The peptide of claim 1, wherein the analog region comprises LQALKALAKALL of seq id no:32.
35. The peptide of claim 1, wherein the analog region comprises QLKALAALAKALL of seq id no:33.
36. The peptide of claim 1, wherein the analog region comprises YKALAALAKKIL of seq id no:34.
37. The peptide of claim 1, wherein the analog region comprises YKALAACAKKIL of seq id no:35.
38. The peptide of claim 1, wherein the analog region comprises YKALCALAKKIL of seq id no:36.
39. The peptide of claim 1, wherein the analog region comprise CNYKALAALAKALL (seq id no:37).
40. The peptide of claim 1, wherein the analog region comprises YKALAALAKALC of seq id no:38.
41. The peptide of claim 1, wherein the analog region comprises LKALAALAKNLL of seq id no:39.
42. The peptide of claim 1, wherein the analog region comprises ILLKALAALAKALL (seq id no:40).
43. The peptide of claim 1, wherein the analog region comprises LRALRALARALL of seq id no:41.
44. The peptide of claim 1, wherein the analog region comprises LKALAALKKALL of seq id no:42.
45. The peptide of claim 1, wherein the analog region comprises WRAWRAWARAWL of seq id no:43.
46. The peptide of claim 1, wherein the analog region comprises LRALAALRRRLL of seq id no:44.
47. The peptide of claim 1, wherein the analog region comprises LKALAALKKKLL of seq id no:45.
48. The peptide of claim 1, wherein the analog region comprises CLLKALAALAKALL (seq id no:46).
49. The peptide of claim 1, wherein the analog region comprises LTAVLLTLLLYRINLKALAALAKALL (seq id no:47).
50. The peptide of claim 1, wherein the peptide comprises a G protein modulator that includes a receptor peptide region having the following structure:

CVYREAKEQIRKIDRVL (Seq id no:48); CVYREAKEQIRKIL (Seq id no:49); IVYREAKEQIRKIDRVL (Seq id no:50); IVYREAKEQIRKIL (Seq id no:51); CIYRETENRARELAALQGSET (Seq id no:52); CIYRETENRARELAALQGSETIL (Seq id no:53); CVYIVAKRTTKNLEAGVMKEIL (Seq id no:54); CVYIVAKRTTKNLEIL (Seq id no:55); CVFQVAKRQLQKIDKVL (Seq id no:56); CPLSYRAKRTPRRAALM (Seq id no:57); CPFRYQSLMTRARAKVI (Seq id no:58); REHKALKTLGIIC (Seq id no:59); CRSPDFRKAFKRLLC (Seq id no:60); CVYREAKEQIRKIDR (Seq id no:61); CISRASKSRIKKDKKEPVAIL (Seq id no:62); CISRASKSRIKKDKKIL (Seq id no:63); CVYVVAKRESRGLKSGLKTDIL (Seq id no:64); or CVYVVAKRESRGLKIL (Seq id no:65).

51. The peptide of claim 50, wherein the receptor peptide region comprises CVYREAKEQIRKIDRVL (seq id no:48).
52. The peptide of claim 50, wherein the receptor peptide region comprises CVYREAKEQIRKIL (seq id no:49).
53. The peptide of claim 50, wherein the receptor peptide region comprises IVYREAKEQIRKIDRVL (seq id no:50).
54. The peptide of claim 50, wherein the receptor peptide region comprises IVYREAKEQIRKIL (seq id no:51).
55. The peptide of claim 50, wherein the receptor peptide region comprises CIYRETENRARELAALQGSET (seq id no:52).

56. The peptide of claim 50, wherein the receptor peptide region comprises CIYRETENRARELAALQGSETIL (seq id no:53).

57. The peptide of claim 50, wherein the receptor peptide region comprises CVYIVAKRTTKNLEAGVMKEIL (seq id no:54).

58. The peptide of claim 50, wherein the receptor peptide region comprises CVYIVAKRTTKNLEIL (seq id no:55).

59. The peptide of claim 50, wherein the receptor peptide region comprises CPLSYRAKRTPRRAALM (seq id no:57).

60. The peptide of claim 50, wherein the receptor peptide region comprises CPFRYQSLMTRARAKVI (seq id no:58).

61. The peptide of claim 50, wherein the receptor peptide region comprises REHKALKTLGIIC (seq id no:59).

62. The peptide of claim 50, wherein the receptor peptide region comprises CRSPDFRKAFKRLLC (seq id no:60).

63. The peptide of claim 50, wherein the receptor peptide region comprises CVYREAKEQIRKIDR (seq id no:61).

64. The peptide of claim 50, wherein the receptor peptide region comprises CISRASKSRIKKDKKEPVAIL (seq id no:62).

65. The peptide of claim 50, wherein the receptor peptide region comprises CISRASKSRIKKDKKIL (seq id no:63).

66. The peptide of claim 50, wherein the receptor peptide region comprises CVYVVAKRESRGLKSGLKTDIL (seq id no:64).

67. The peptide of claim 50, wherein the receptor peptide region comprises CVYVVAKRESRGLKIL (seq id no:65).

68. The peptide of claim 1, wherein the first two amino terminal amino acids comprise hydrophobic amino acids.

69. The peptide of claim 68, wherein the first two amino terminal amino acids comprise I, L or V.

70. The peptide of claim 1, amidated at its carboxy terminus.

71. The peptide of claim 1, acylated at its amino terminus.

72. The peptide of claim 71, wherein the acylated amino terminus is acylated through an amino terminal cysteine residue.

73. The peptide of claim 71, wherein the amino terminus is acylated with a C-10 to C-22 alkyl group.

74. The peptide of claim 73, wherein the amino terminus is alkylated with a C-12 to C-16 alkyl group.

75. The peptide of claim 1, comprising a hydrophobic C-terminus.

76. The peptide of claim 75, wherein hydrophobic C-terminus comprises a hydrophobic dipeptide region.

77. The peptide of claim 76, wherein the hydrophobic dipeptide region comprises I, V or L residues.

78. The peptide of claim 1, wherein at least one amino acid of said analog comprises a D-isomer.

79. The peptide of claim 1, further defined as capable of activating a G-protein.

80. The peptide of claim 1, wherein $AA_2$, $AA_9$ or $AA_{10}$ comprises alanine, glutamine or arginine.

81. The peptide of claim 80, wherein $A_{10}$ comprises alanine.

82. The peptide of claim 80, wherein more than one of $AA_2$, $AA_9$ and $AA_{10}$ comprises alanine, glutamine or arginine.

83. A pharmacologic composition comprising a therapeutically effective amount of a peptide comprising a mastoparan analog in accordance with claim 1, dispersed in a pharmacologically acceptable carrier or diluent.

84. The composition of claim 83, wherein the analog is dispersed in a carrier adapted for topical administration.

85. The peptide of claim 50, wherein the receptor peptide region comprises CVFQVAKRQLQKIDKVL (Seq id no:56).

* * * * *

SEQUENCE LISTING ( 1 ) GENERAL INFORMATION:

( i i i ) NUMBER OF SEQUENCES: 71

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Ile  Asn  Leu  Lys  Ala  Leu  Ala  Ala  Leu  Ala  Lys  Lys  Leu  Leu
 1                    5                         10
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Ile  Asn  Leu  Lys  Ala  Leu  Ala  Ala  Leu  Ala  Lys  Lys  Leu  Ala
 1                    5                         10
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

Ile Asn Leu Lys Ala Leu Ala Ala Leu Ala Lys Lys Ala Leu
1               5                   10

( 2 ) INFORMATION FOR SEQ ID NO:4:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( x i ) SEQUENCE DESCRIPTION: SEQ ID NO:4:

Ile Asn Leu Lys Ala Leu Ala Ala Leu Ala Lys Lys Lys Leu
1               5                   10

( 2 ) INFORMATION FOR SEQ ID NO:5:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( x i ) SEQUENCE DESCRIPTION: SEQ ID NO:5:

Ile Asn Leu Lys Ala Leu Ala Ala Leu Ala Lys Ala Leu Leu
1               5                   10

( 2 ) INFORMATION FOR SEQ ID NO:6:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( x i ) SEQUENCE DESCRIPTION: SEQ ID NO:6:

Ile Asn Leu Lys Ala Leu Ala Ala Leu Ala Lys Arg Leu Leu
1               5                   10

( 2 ) INFORMATION FOR SEQ ID NO:7:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( x i ) SEQUENCE DESCRIPTION: SEQ ID NO:7:

Ile Asn Leu Lys Ala Leu Ala Ala Leu Ala Ala Lys Leu Leu
1               5                   10

( 2 ) INFORMATION FOR SEQ ID NO:8:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( x i ) SEQUENCE DESCRIPTION: SEQ ID NO:8:

Ile Asn Leu Lys Ala Leu Ala Ala Leu Ala Arg Lys Leu Leu
1               5                   10

( 2 ) INFORMATION FOR SEQ ID NO:9:

( i ) SEQUENCE CHARACTERISTICS:

(A) LENGTH: 14 amino acids
(B) TYPE: amino acid
(C) STRANDEDNESS: single
(D) TOPOLOGY: linear (xi) SEQUENCE DESCRIPTION: SEQ ID NO:9:

Ile Asn Leu Lys Ala Leu Ala Ala Leu Lys Lys Lys Leu Leu
 1               5                   10

(2) INFORMATION FOR SEQ ID NO:10:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO:10:

Ile Asn Leu Lys Ala Leu Ala Ala Ala Ala Lys Lys Leu Leu
 1               5                   10

(2) INFORMATION FOR SEQ ID NO:11:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO:11:

Ile Asn Leu Lys Ala Leu Ala Ala Lys Ala Lys Lys Leu Leu
 1               5                   10

(2) INFORMATION FOR SEQ ID NO:12:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO:12:

Ile Asn Leu Lys Ala Leu Ala Lys Leu Ala Lys Lys Leu Leu
 1               5                   10

(2) INFORMATION FOR SEQ ID NO:13:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO:13:

Ile Asn Leu Lys Ala Leu Lys Ala Leu Ala Lys Lys Leu Leu
 1               5                   10

(2) INFORMATION FOR SEQ ID NO:14:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO:14:

Ile Asn Leu Lys Ala Ala Ala Ala Leu Ala Lys Lys Leu Leu
 1               5                   10

(2) INFORMATION FOR SEQ ID NO:15:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:15:

Ile Asn Leu Lys Ala Lys Ala Ala Leu Ala Lys Lys Leu Leu
   1               5                   10

(2) INFORMATION FOR SEQ ID NO:16:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:16:

Ile Asn Leu Lys Lys Leu Ala Ala Leu Ala Lys Lys Leu Leu
   1               5                   10

(2) INFORMATION FOR SEQ ID NO:17:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:17:

Ile Asn Leu Ala Ala Leu Ala Ala Leu Ala Lys Lys Leu Leu
   1               5                   10

(2) INFORMATION FOR SEQ ID NO:18:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:18:

Ile Asn Leu Arg Ala Leu Ala Ala Leu Ala Lys Lys Leu Leu
   1               5                   10

(2) INFORMATION FOR SEQ ID NO:19:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:19:

Ile Asn Ala Lys Ala Leu Ala Ala Leu Ala Lys Lys Leu Leu
   1               5                   10

(2) INFORMATION FOR SEQ ID NO:20:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:20:

```
Ile  Asn  Phe  Lys  Ala  Leu  Ala  Ala  Leu  Ala  Lys  Lys  Leu  Leu
 1              5                        10
```

(2) INFORMATION FOR SEQ ID NO:21:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:21:

```
Ile  Asn  Leu  Lys  Ala  Phe  Ala  Ala  Leu  Ala  Lys  Lys  Leu  Leu
 1              5                        10
```

(2) INFORMATION FOR SEQ ID NO:22:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:22:

```
Ile  Asn  Leu  Lys  Ala  Leu  Ala  Ala  Leu  Ala  Lys  Ala  Leu  Leu
 1              5                        10
```

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:23:

```
Ile  Asn  Leu  Lys  Ala  Leu  Ala  Ala  Leu  Ala  Arg  Ala  Leu  Leu
 1              5                        10
```

(2) INFORMATION FOR SEQ ID NO:24:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:24:

```
Ile  Asn  Leu  Lys  Ala  Leu  Ala  Ala  Leu  Ala  Gln  Ala  Leu  Leu
 1              5                        10
```

(2) INFORMATION FOR SEQ ID NO:25:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:25:

```
Ile  Asn  Leu  Ala  Ala  Leu  Ala  Ala  Leu  Ala  Lys  Ala  Leu  Leu
 1              5                        10
```

(2) INFORMATION FOR SEQ ID NO:26:

(i) SEQUENCE CHARACTERISTICS:
        (A) LENGTH: 14 amino acids
        (B) TYPE: amino acid (C) STRANDEDNESS: single
(D) TOPOLOGY: linear ( x i ) SEQUENCE DESCRIPTION: SEQ ID NO:26:

Ile Asn Leu Lys Ala Leu Ala Ala Leu Ala Ala Ala Leu Leu
1               5                   10

( 2 ) INFORMATION FOR SEQ ID NO:27:

( i ) SEQUENCE CHARACTERISTICS:
(A) LENGTH: 14 amino acids
(B) TYPE: amino acid
(C) STRANDEDNESS: single
(D) TOPOLOGY: linear ( x i ) SEQUENCE DESCRIPTION: SEQ ID NO:27:

Ile Asn Leu Arg Ala Leu Ala Ala Leu Ala Lys Ala Leu Leu
1               5                   10

( 2 ) INFORMATION FOR SEQ ID NO:28:

( i ) SEQUENCE CHARACTERISTICS:
(A) LENGTH: 14 amino acids
(B) TYPE: amino acid
(C) STRANDEDNESS: single
(D) TOPOLOGY: linear ( x i ) SEQUENCE DESCRIPTION: SEQ ID NO:28:

Ile Asn Leu Arg Ala Leu Ala Ala Leu Ala Arg Ala Leu Leu
1               5                   10

( 2 ) INFORMATION FOR SEQ ID NO:29:

( i ) SEQUENCE CHARACTERISTICS:
(A) LENGTH: 14 amino acids
(B) TYPE: amino acid
(C) STRANDEDNESS: single
(D) TOPOLOGY: linear ( x i ) SEQUENCE DESCRIPTION: SEQ ID NO:29:

Ile Asn Leu Gln Ala Leu Ala Ala Leu Ala Lys Ala Leu Leu
1               5                   10

( 2 ) INFORMATION FOR SEQ ID NO:30:

( i ) SEQUENCE CHARACTERISTICS:
(A) LENGTH: 14 amino acids
(B) TYPE: amino acid
(C) STRANDEDNESS: single
(D) TOPOLOGY: linear ( x i ) SEQUENCE DESCRIPTION: SEQ ID NO:30:

Ile Asn Leu Gln Ala Leu Ala Ala Leu Ala Gln Ala Leu Leu
1               5                   10

( 2 ) INFORMATION FOR SEQ ID NO:31:

( i ) SEQUENCE CHARACTERISTICS:
(A) LENGTH: 14 amino acids
(B) TYPE: amino acid
(C) STRANDEDNESS: single
(D) TOPOLOGY: linear ( x i ) SEQUENCE DESCRIPTION: SEQ ID NO:31:

Ile Asn Leu Lys Ala Leu Lys Ala Leu Ala Lys Ala Leu Leu
1               5                   10

( 2 ) INFORMATION FOR SEQ ID NO:32:

( i ) SEQUENCE CHARACTERISTICS:
   ( A ) LENGTH: 14 amino acids
   ( B ) TYPE: amino acid
   ( C ) STRANDEDNESS: single
   ( D ) TOPOLOGY: linear ( x i ) SEQUENCE DESCRIPTION: SEQ ID NO:32:

Ile Asn Leu Gln Ala Leu Lys Ala Leu Ala Lys Ala Leu Leu
 1               5                   10

( 2 ) INFORMATION FOR SEQ ID NO:33:

( i ) SEQUENCE CHARACTERISTICS:
   ( A ) LENGTH: 14 amino acids
   ( B ) TYPE: amino acid
   ( C ) STRANDEDNESS: single
   ( D ) TOPOLOGY: linear ( x i ) SEQUENCE DESCRIPTION: SEQ ID NO:33:

Ile Gln Leu Lys Ala Leu Ala Ala Leu Ala Lys Ala Leu Leu
 1               5                   10

( 2 ) INFORMATION FOR SEQ ID NO:34:

( i ) SEQUENCE CHARACTERISTICS:
   ( A ) LENGTH: 14 amino acids
   ( B ) TYPE: amino acid
   ( C ) STRANDEDNESS: single
   ( D ) TOPOLOGY: linear ( x i ) SEQUENCE DESCRIPTION: SEQ ID NO:34:

Ile Asn Tyr Lys Ala Leu Ala Ala Leu Ala Lys Lys Ile Leu
 1               5                   10

( 2 ) INFORMATION FOR SEQ ID NO:35:

( i ) SEQUENCE CHARACTERISTICS:
   ( A ) LENGTH: 14 amino acids
   ( B ) TYPE: amino acid
   ( C ) STRANDEDNESS: single
   ( D ) TOPOLOGY: linear ( x i ) SEQUENCE DESCRIPTION: SEQ ID NO:35:

Ile Asn Tyr Lys Ala Leu Ala Ala Cys Ala Lys Lys Ile Leu
 1               5                   10

( 2 ) INFORMATION FOR SEQ ID NO:36:

( i ) SEQUENCE CHARACTERISTICS:
   ( A ) LENGTH: 14 amino acids
   ( B ) TYPE: amino acid
   ( C ) STRANDEDNESS: single
   ( D ) TOPOLOGY: linear ( x i ) SEQUENCE DESCRIPTION: SEQ ID NO:36:

Ile Asn Tyr Lys Ala Leu Cys Ala Leu Ala Lys Lys Ile Leu
 1               5                   10

( 2 ) INFORMATION FOR SEQ ID NO:37:

( i ) SEQUENCE CHARACTERISTICS:
   ( A ) LENGTH: 14 amino acids
   ( B ) TYPE: amino acid
   ( C ) STRANDEDNESS: single
   ( D ) TOPOLOGY: linear ( x i ) SEQUENCE DESCRIPTION: SEQ ID NO:37:

Cys Asn Tyr Lys Ala Leu Ala Ala Leu Ala Lys Ala Leu Leu ( 2 ) INFORMATION FOR SEQ ID NO:38:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:38:

```
Ile Asn Tyr Lys Ala Leu Ala Ala Leu Ala Lys Ala Leu Cys
 1               5                  10
```

( 2 ) INFORMATION FOR SEQ ID NO:39:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:39:

```
Ile Asn Leu Lys Ala Leu Ala Ala Leu Ala Lys Asn Leu Leu
 1               5                  10
```

( 2 ) INFORMATION FOR SEQ ID NO:40:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:40:

```
Ile Leu Leu Lys Ala Leu Ala Ala Leu Ala Lys Ala Leu Leu
 1               5                  10
```

( 2 ) INFORMATION FOR SEQ ID NO:41:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:41:

```
Ile Asn Leu Arg Ala Leu Arg Ala Leu Ala Arg Ala Leu Leu
 1               5                  10
```

( 2 ) INFORMATION FOR SEQ ID NO:42:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:42:

```
Ile Asn Leu Lys Ala Leu Ala Ala Leu Lys Lys Ala Leu Leu
 1               5                  10
```

( 2 ) INFORMATION FOR SEQ ID NO:43:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:43:

Ile Asn Trp Arg Ala Trp Arg Ala Trp Ala Arg Ala Trp Leu
 1               5                          10

( 2 ) INFORMATION FOR SEQ ID NO:44:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:44:

Ile Asn Leu Arg Ala Leu Ala Ala Leu Arg Arg Arg Leu Leu
 1               5                          10

( 2 ) INFORMATION FOR SEQ ID NO:45:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:45:

Ile Asn Leu Lys Ala Leu Ala Ala Leu Lys Lys Lys Leu Leu
 1               5                          10

( 2 ) INFORMATION FOR SEQ ID NO:46:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:46:

Cys Leu Leu Lys Ala Leu Ala Ala Leu Ala Lys Ala Leu Leu
 1               5                          10

( 2 ) INFORMATION FOR SEQ ID NO:47:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( x i ) SEQUENCE DESCRIPTION: SEQ ID NO:47:

Leu Thr Ala Val Leu Leu Thr Leu Leu Leu Tyr Arg Ile Asn Leu
 1               5                          10                          15

Lys Ala Leu Ala Ala Leu Ala Lys Ala Leu Leu
                    20                          25

( 2 ) INFORMATION FOR SEQ ID NO:48:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:48:

Cys Val Tyr Arg Glu Ala Lys Glu Gln Ile Arg Lys Ile Asp Arg
 1               5                          10                          15

Val Leu ( 2 ) INFORMATION FOR SEQ ID NO:49:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:49:

```
Cys Val Tyr Arg Glu Ala Lys Glu Gln Ile Arg Lys Ile Leu
 1               5                  10
```

( 2 ) INFORMATION FOR SEQ ID NO:50:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:50:

```
Ile Val Tyr Arg Glu Ala Lys Glu Gln Ile Arg Lys Ile Asp Arg
 1               5                  10                  15
Val Leu
```

( 2 ) INFORMATION FOR SEQ ID NO:51:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:51:

```
Ile Val Tyr Arg Glu Ala Lys Glu Gln Ile Arg Lys Ile Leu
 1               5                  10
```

( 2 ) INFORMATION FOR SEQ ID NO:52:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( x i ) SEQUENCE DESCRIPTION: SEQ ID NO:52:

```
Cys Ile Tyr Arg Glu Thr Glu Asn Arg Ala Arg Glu Leu Ala Ala
 1               5                  10                  15
Leu Gln Gly Ser Glu Thr
                 20
```

( 2 ) INFORMATION FOR SEQ ID NO:53:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( x i ) SEQUENCE DESCRIPTION: SEQ ID NO:53:

```
Cys Ile Tyr Arg Glu Thr Glu Asn Arg Ala Arg Glu Leu Ala Ala
 1               5                  10                  15
Leu Gln Gly Ser Glu Thr Ile Leu
                 20
```

( 2 ) INFORMATION FOR SEQ ID NO:54:

( i ) SEQUENCE CHARACTERISTICS:
          ( A ) LENGTH: 22 amino acids
          ( B ) TYPE: amino acid
          ( C ) STRANDEDNESS: single
          ( D ) TOPOLOGY: linear ( x i ) SEQUENCE DESCRIPTION: SEQ ID NO:54:

```
Cys  Val  Tyr  Ile  Val  Ala  Lys  Arg  Thr  Thr  Lys  Asn  Leu  Glu  Ala
 1                  5                        10                       15

Gly  Val  Met  Lys  Glu  Ile  Leu
                    20
```

( 2 ) INFORMATION FOR SEQ ID NO:55:

( i ) SEQUENCE CHARACTERISTICS:
          ( A ) LENGTH: 16 amino acids
          ( B ) TYPE: amino acid
          ( C ) STRANDEDNESS: single
          ( D ) TOPOLOGY: linear ( x i ) SEQUENCE DESCRIPTION: SEQ ID NO:55:

```
Cys  Val  Tyr  Ile  Val  Ala  Lys  Arg  Thr  Thr  Lys  Asn  Leu  Glu  Ile
 1                  5                        10                       15

Leu
```

( 2 ) INFORMATION FOR SEQ ID NO:56:

( i ) SEQUENCE CHARACTERISTICS:
          ( A ) LENGTH: 17 amino acids
          ( B ) TYPE: amino acid
          ( C ) STRANDEDNESS: single
          ( D ) TOPOLOGY: linear ( x i ) SEQUENCE DESCRIPTION: SEQ ID NO:56:

```
Cys  Val  Phe  Gln  Val  Ala  Lys  Arg  Gln  Leu  Gln  Lys  Ile  Asp  Lys
 1                  5                        10                       15

Val  Leu
```

( 2 ) INFORMATION FOR SEQ ID NO:57:

( i ) SEQUENCE CHARACTERISTICS:
          ( A ) LENGTH: 17 amino acids
          ( B ) TYPE: amino acid
          ( C ) STRANDEDNESS: single
          ( D ) TOPOLOGY: linear ( x i ) SEQUENCE DESCRIPTION: SEQ ID NO:57:

```
Cys  Pro  Leu  Ser  Tyr  Arg  Ala  Lys  Arg  Thr  Pro  Arg  Arg  Ala  Ala
 1                  5                        10                       15

Leu  Met
```

( 2 ) INFORMATION FOR SEQ ID NO:58:

( i ) SEQUENCE CHARACTERISTICS:
          ( A ) LENGTH: 17 amino acids
          ( B ) TYPE: amino acid
          ( C ) STRANDEDNESS: single
          ( D ) TOPOLOGY: linear ( x i ) SEQUENCE DESCRIPTION: SEQ ID NO:58:

```
Cys  Pro  Phe  Arg  Tyr  Gln  Ser  Leu  Met  Thr  Arg  Ala  Arg  Ala  Lys
 1                  5                        10                       15

Val  Ile
```

( 2 ) INFORMATION FOR SEQ ID NO:59:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( x i ) SEQUENCE DESCRIPTION: SEQ ID NO:59:

```
Arg  Glu  His  Lys  Ala  Leu  Lys  Thr  Leu  Gly  Ile  Ile  Cys
 1              5                        10
```

( 2 ) INFORMATION FOR SEQ ID NO:60:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( x i ) SEQUENCE DESCRIPTION: SEQ ID NO:60:

```
Cys  Arg  Ser  Pro  Asp  Phe  Arg  Lys  Ala  Phe  Lys  Arg  Leu  Leu  Cys
 1              5                        10                         15
```

( 2 ) INFORMATION FOR SEQ ID NO:61:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( x i ) SEQUENCE DESCRIPTION: SEQ ID NO:61:

```
Cys  Val  Tyr  Arg  Glu  Ala  Lys  Glu  Gln  Ile  Arg  Lys  Ile  Asp  Arg
 1              5                        10                         15
```

( 2 ) INFORMATION FOR SEQ ID NO:62:

( i ) SEQUENCE CHARACTERISTICS:
      ( A ) LENGTH: 21 amino acids
      ( B ) TYPE: amino acid
      ( C ) STRANDEDNESS: single
      ( D ) TOPOLOGY: linear ( x i ) SEQUENCE DESCRIPTION: SEQ ID NO:62:

```
Cys  Ile  Ser  Arg  Ala  Ser  Lys  Ser  Arg  Ile  Lys  Lys  Asp  Lys  Lys
 1              5                        10                         15

Glu  Pro  Val  Ala  Ile  Leu
                20
```

( 2 ) INFORMATION FOR SEQ ID NO:63:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( x i ) SEQUENCE DESCRIPTION: SEQ ID NO:63:

```
Cys  Ile  Ser  Arg  Ala  Ser  Lys  Ser  Arg  Ile  Lys  Lys  Asp  Lys  Lys
 1              5                        10                         15

Ile  Leu
```

( 2 ) INFORMATION FOR SEQ ID NO:64:

( i ) SEQUENCE CHARACTERISTICS:
      ( A ) LENGTH: 22 amino acids ( B ) TYPE: amino acid
( C ) STRANDEDNESS: single
( D ) TOPOLOGY: linear ( x i ) SEQUENCE DESCRIPTION: SEQ ID NO:64:

Cys Val Tyr Val Val Ala Lys Arg Glu Ser Arg Gly Leu Lys Ser
1               5                   10                  15

Gly Leu Lys Thr Asp Ile Leu
                20

( 2 ) INFORMATION FOR SEQ ID NO:65:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( x i ) SEQUENCE DESCRIPTION: SEQ ID NO:65:

Cys Val Tyr Val Val Ala Lys Arg Glu Ser Arg Gly Leu Lys Ile
1               5                   10                  15

Leu ( 2 ) INFORMATION FOR SEQ ID NO:66:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( x i ) SEQUENCE DESCRIPTION: SEQ ID NO:66:

Ile Asn Leu Lys Ala Leu Ala Ala Leu Ala Lys Lys Ile Leu
1               5                   10

( 2 ) INFORMATION FOR SEQ ID NO:67:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( x i ) SEQUENCE DESCRIPTION: SEQ ID NO:67:

Ile Lys Trp Lys Ala Ile Leu Asp Ala Val Lys Lys Val Leu
1               5                   10

( 2 ) INFORMATION FOR SEQ ID NO:68:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( x i ) SEQUENCE DESCRIPTION: SEQ ID NO:68:

Ile Asn Leu Lys Ala Ile Ala Ala Phe Ala Lys Lys Leu Leu
1               5                   10

( 2 ) INFORMATION FOR SEQ ID NO:69:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( x i ) SEQUENCE DESCRIPTION: SEQ ID NO:69:

Ile Asn Trp Lys Gly Ile Ala Ala Met Ala Lys Lys Leu Leu
 1               5                        10

(2) INFORMATION FOR SEQ ID NO: 70:

(i) SEQUENCE CHARACTERISTICS:
        (A) LENGTH: 12 amino acids
        (B) TYPE: amino acid
        (C) STRANDEDNESS:
        (D) TOPOLOGY: linear (ix) FEATURE:
        (A) NAME/KEY: Modified-site
        (B) LOCATION:1
        (D) OTHER INFORMATION:/product= "OTHER"
            /note= "Xaa = Leucine, Tryptophan, Alanine,
            Phenylalanine or Tyrosine"

(ix) FEATURE:
        (A) NAME/KEY: Modified-site
        (B) LOCATION:2
        (D) OTHER INFORMATION:/product= "OTHER"
            /note= "Xaa = Lysine, Alanine, Arginine
            or Glutamine"

(ix) FEATURE:
        (A) NAME/KEY: Modified-site
        (B) LOCATION:3
        (D) OTHER INFORMATION:/product= "OTHER"
            /note= "Xaa = Alanine or Lysine"

(ix) FEATURE:
        (A) NAME/KEY: Modified-site
        (B) LOCATION:4
        (D) OTHER INFORMATION:/product= "OTHER"
            /note= "Xaa = Leucine, Tryptophan, Isoleucine,
            Alanine, Lysine or Phenylalanine"

(ix) FEATURE:
        (A) NAME/KEY: Modified-site
        (B) LOCATION:5
        (D) OTHER INFORMATION:/product= "OTHER"
            /note= "Xaa = Alanine, Leucine, Lysine, Cysteine
            or Arginine"

(ix) FEATURE:
        (A) NAME/KEY: Modified-site
        (B) LOCATION:6
        (D) OTHER INFORMATION:/product= "OTHER"
            /note= "Xaa = Alanine, Aspartic acid or Lysine"

(ix) FEATURE:
        (A) NAME/KEY: Modified-site
        (B) LOCATION:7
        (D) OTHER INFORMATION:/product= "OTHER"
            /note= "Xaa = Leucine, Cysteine, Tryptophan,
            Alanine, Phenylalanine or Lysine"

(ix) FEATURE:
        (A) NAME/KEY: Modified-site
        (B) LOCATION:8
        (D) OTHER INFORMATION:/product= "OTHER"
            /note= "Xaa = Alanine, Valine, Lysine or Arginine"

(ix) FEATURE:
        (A) NAME/KEY: Modified-site
        (B) LOCATION:9
        (D) OTHER INFORMATION:/product= "OTHER"
            /note= "Xaa = Lysine, Arginine, Glutamine or
            Alanine"

(ix) FEATURE:
        (A) NAME/KEY: Modified-site
        (B) LOCATION:10
        (D) OTHER INFORMATION:/product= "OTHER"
            /note= "Xaa = Lysine, Alanine, Arginine or
            Asparagine"

( i x ) FEATURE:
 ( A ) NAME/KEY: Modified-site
 ( B ) LOCATION:11
 ( D ) OTHER INFORMATION:/product= "OTHER"
  / note= "Xaa = Leucine, Isoleucine, Tryptophan, Valine, Alanine or Lysine"

( i x ) FEATURE:
 ( A ) NAME/KEY: Modified-site
 ( B ) LOCATION:12
 ( D ) OTHER INFORMATION:/product= "OTHER"
  / note= "Xaa = Leucine, Alanine or Cysteine"

( x i ) SEQUENCE DESCRIPTION: SEQ ID NO: 70:

Xaa Xaa Xaa Xaa Xaa Xaa Xaa Xaa Xaa Xaa Xaa Xaa
1               5                           10

( 2 ) INFORMATION FOR SEQ ID NO: 71:

( i ) SEQUENCE CHARACTERISTICS:
  ( A ) LENGTH: 14 amino acids
  ( B ) TYPE: amino acid
  ( C ) STRANDEDNESS:
  ( D ) TOPOLOGY: linear ( i x ) FEATURE:
 ( A ) NAME/KEY: Modified-site
 ( B ) LOCATION:1
 ( D ) OTHER INFORMATION:/product= "OTHER"
  / note= "Xaa = Isoleucine or Cysteine"

( i x ) FEATURE:
 ( A ) NAME/KEY: Modified-site
 ( B ) LOCATION:2
 ( D ) OTHER INFORMATION:/product= "OTHER"
  / note= "Xaa = Asparagine, Lysine, Glutamine or Leucine"

( i x ) FEATURE:
 ( A ) NAME/KEY: Modified-site
 ( B ) LOCATION:3
 ( D ) OTHER INFORMATION:/product= "OTHER"
  / note= "Xaa = Leucine, Tryptophan, Alanine, Phenylalanine or Tyrosine"

( i x ) FEATURE:
 ( A ) NAME/KEY: Modified-site
 ( B ) LOCATION:4
 ( D ) OTHER INFORMATION:/product= "OTHER"
  / note= "Xaa = Lysine, Alanine, Arginine or Glutamine"

( i x ) FEATURE:
 ( A ) NAME/KEY: Modified-site
 ( B ) LOCATION:5
 ( D ) OTHER INFORMATION:/product= "OTHER"
  / note= "Xaa = Alanine or Lysine"

( i x ) FEATURE:
 ( A ) NAME/KEY: Modified-site
 ( B ) LOCATION:6
 ( D ) OTHER INFORMATION:/product= "OTHER"
  / note= "Xaa = Leucine, Tryptophan, Isoleucine, Alanine, Lysine or Phenylalanine"

( i x ) FEATURE:
 ( A ) NAME/KEY: Modified-site
 ( B ) LOCATION:7
 ( D ) OTHER INFORMATION:/product= "OTHER"
  / note= "Xaa = Alanine, Leucine, Lysine, Cysteine or Arginine"

( i x ) FEATURE:
 ( A ) NAME/KEY: Modified-site
 ( B ) LOCATION:8
 ( D ) OTHER INFORMATION:/product= "OTHER"
  / note= "Xaa = Alanine, Aspartic acid or Lysine"

(ix) FEATURE:
    (A) NAME/KEY: Modified-site
    (B) LOCATION: 9
    (D) OTHER INFORMATION: /product= "OTHER"
        /note= "Xaa = Leucine, Cysteine, Tryptophan, Alanine, Phenylalanine or Lysine"

(ix) FEATURE:
    (A) NAME/KEY: Modified-site
    (B) LOCATION: 10
    (D) OTHER INFORMATION: /product= "OTHER"
        /note= "Xaa = Alanine, Valine, Lysine or Arginine"

(ix) FEATURE:
    (A) NAME/KEY: Modified-site
    (B) LOCATION: 11
    (D) OTHER INFORMATION: /product= "OTHER"
        /note= "Xaa = Lysine, Arginine, Glutamine or Alanine"

(ix) FEATURE:
    (A) NAME/KEY: Modified-site
    (B) LOCATION: 12
    (D) OTHER INFORMATION: /product= "OTHER"
        /note= "Xaa = Lysine, Alanine, Arginine or Asparagine"

(ix) FEATURE:
    (A) NAME/KEY: Modified-site
    (B) LOCATION: 13
    (D) OTHER INFORMATION: /product= "OTHER"
        /note= "Xaa = Leucine, Isoleucine, Tryptophan, Valine, Alanine or Lysine"

(ix) FEATURE:
    (A) NAME/KEY: Modified-site
    (B) LOCATION: 14
    (D) OTHER INFORMATION: /product= "OTHER"
        /note= "Xaa = Leucine, Alanine or Cysteine"

(xi) SEQUENCE DESCRIPTION: SEQ ID NO: 71:

Xaa Xaa Xaa Xaa Xaa Xaa Xaa Xaa Xaa Xaa Xaa Xaa Xaa Xaa
 1               5                          10